United States Patent
Aihara et al.

(10) Patent No.: US 10,370,696 B2
(45) Date of Patent: Aug. 6, 2019

(54) METHOD FOR CELL RECOVERY

(71) Applicant: NISSAN CHEMICAL INDUSTRIES, LTD., Tokyo (JP)

(72) Inventors: Ayako Aihara, Shiraoka (JP); Taito Nishino, Shiraoka (JP)

(73) Assignee: NISSAN CHEMICAL INDUSTRIES, LTD., Tokyo (JP)

( * ) Notice: Subject to any disclaimer, the term of this patent is extended or adjusted under 35 U.S.C. 154(b) by 47 days.

(21) Appl. No.: 15/509,140

(22) PCT Filed: Sep. 9, 2015

(86) PCT No.: PCT/JP2015/075646
§ 371 (c)(1),
(2) Date: Mar. 6, 2017

(87) PCT Pub. No.: WO2016/039391
PCT Pub. Date: Mar. 17, 2016

(65) Prior Publication Data
US 2017/0253907 A1    Sep. 7, 2017

(30) Foreign Application Priority Data

Sep. 9, 2014  (JP) .................................. 2014-183687
May 29, 2015  (JP) .................................. 2015-110331

(51) Int. Cl.
*C12N 5/00*    (2006.01)
*C12Q 1/24*    (2006.01)
*C12N 5/07*    (2010.01)

(52) U.S. Cl.
CPC .................. *C12Q 1/24* (2013.01); *C12N 5/00* (2013.01); *C12N 5/06* (2013.01); *C12N 2500/34* (2013.01)

(58) Field of Classification Search
None
See application file for complete search history.

(56) References Cited

U.S. PATENT DOCUMENTS

| 2016/0060601 A1 | 3/2016 | Nishino et al. |
| 2017/0002311 A1 | 1/2017 | Otani et al. |

FOREIGN PATENT DOCUMENTS

| EP | 2878664 | * | 6/2015 | ............... C12N 1/00 |
| EP | 2878664 A1 | | 6/2015 | |
| WO | WO 2014/017513 A1 | | 1/2014 | |
| WO | WO 2014/171486 A1 | | 10/2014 | |
| WO | WO 2015/111685 A1 | | 7/2015 | |

OTHER PUBLICATIONS

Camelin et al, "Effect of Chelatants on Gellan Gel Rheological Properties and Setting Temperature for Immobilization of Living Bifidobacteria" Biotechnology Progress, 1993, vol. 9, pp. 291-297. (Year: 1993).*
Eyre et al, "Sterile Culture of Rotylenchulus reniformis on Tomato Root with Gellan Gum as a Supporting Medium" Journal of Nematology, 1991, vol. 23, No. 2, pp. 229-231. (Year: 1991).*
"Gelzan CM" from Sigma-Aldrich Online Product catalog. Retrieved from URL: https://www.sigmaaldrich.com/catalog/product/sigma/g1910?lang=en&region=US (Year: 2018).*
Francis et al., "Isolating adipose-derived mesenchymal stem cells from lipoaspirate blood and saline fraction," *Organogenesis*, 6(1): 11-14 (2010).
Japanese Patent Office, International Search Report in International Patent Application No. PCT/JP2015/075646 (dated Nov. 17, 2015) English translation.

* cited by examiner

*Primary Examiner* — Allison M Fox
(74) *Attorney, Agent, or Firm* — Leydig, Voit & Mayer, Ltd.

(57) ABSTRACT

The present invention provides a method of isolating cells or tissues from a culture preparation of the cells or tissues in a medium composition which enables culture of the cells or tissues in suspension, which comprises at least one step selected from the group consisting of the following (A), (B) and (C):
(A) passing the culture preparation through a filter having fine pores having a pore diameter of 5-500 μm,
(B) adding a chelator to the culture preparation, and
(C) diluting the culture preparation with a physiological aqueous solution.

20 Claims, No Drawings

METHOD FOR CELL RECOVERY

CROSS-REFERENCE TO RELATED APPLICATIONS

This patent application is the U.S. national phase of International Patent Application No. PCT/JP2015/075646, filed on Sep. 9, 2015, which claims the benefit of Japanese Patent Application No. 2014-183687, filed on Sep. 9, 2014, and Japanese Patent Application No. 2015-110331, filed on May 29, 2015, the disclosures of which are incorporated herein by reference in their entireties for all purposes.

TECHNICAL FIELD

The present invention relates to a method of recovering cells and/or tissues of animals or plants from a medium composition which enables culture in three dimensions or in a suspended state.

BACKGROUND ART

In recent years, techniques for proliferating or maintaining in vitro various organs, tissues and cells that play distinct roles in the body of animals and plants have been developed. Proliferation or maintenance of the organs and tissues in vitro is called organ culture and tissue culture, respectively, and proliferating, differentiating or maintaining in vitro the cells separated from an organ or tissue is called cell culture. Cell culture is a technique for proliferating, differentiating or maintaining separated cells in vitro in a medium, and is indispensable for detailed analyses of the in vivo function and structure of various organs, tissues and cells. In addition, the cells and/or tissues cultured by the technique are utilized in various fields for efficacy and toxicity evaluation of chemical substances, pharmaceutical products and the like, large-scale production of useful substances such as enzymes, cell growth factors, antibodies and the like, regenerative medicine supplementing organ, tissue and cell that were lost by disease and deficiency, improvement of plant brand, production of genetically modified products, and the like.

Animal-derived cells are broadly divided into non-adherent cells and adherent cells based on the properties thereof. Non-adherent cells are cells that do not require a scaffold for growth and proliferation, and adherent cells are cells that require a scaffold for growth and proliferation. Most of the cells constituting the living body are the latter, adherent cells. As culture methods of adherent cells, single layer culture, dispersion culture, embedded culture, microcarrier culture, sphere culture and the like are known.

It has been reported that static state suspension culture of animal and plant cells and/or tissues can be performed by mixing a structure containing a polymer compound having an anionic functional group, such as deacylated gellan gum and the like in a liquid medium, without substantially increasing the viscosity of the liquid medium and that the proliferation activity of the cells is promoted by culture using this medium composition containing the above-mentioned structure (patent document 1). In the medium composition, a polymer compound having an anionic functional group, such as deacylated gellan gum and the like, is linked via a metal ion (e.g., divalent metal ion such as calcium ion and the like) to form an indeterminate structure, which in turn forms a three dimensional network in the medium to provide a carrier for suspending cells and the like.

DOCUMENT LIST

Patent Documents patent document 1: WO 2014/017513

SUMMARY OF THE INVENTION

Problems to be Solved by the Invention

As mentioned above, it has been reported that static state suspension culture of animal and plant cells and/or tissues can be performed by mixing a structure comprising a polymer compound having an anionic functional group, such as deacylated gellan gum and the like, in a liquid medium, without substantially increasing the viscosity of the liquid medium, and that the growth activity of the cell is promoted by culture using this medium composition. The present inventors have found a new problem of collecting animal and plant cells and/or tissues more efficiently after culturing the animal and plant cells and/or tissues in the medium composition.

The present invention aims to provide a method of collecting (recovering) animal and plant cells and/or tissues more efficiently after culturing the animal and plant cells and/or tissues by using the medium composition, and the like.

Means of Solving the Problems

The present inventors have conducted intensive studies in an attempt to solve the above-mentioned problems, and found that the recovery rate of the cells and/or tissues is improved by a pre-treatment including passing a medium composition after culture of animal and plant cells and/or tissues through a filter having fine pores with a size of 5-500 μm, through which the cells and/or tissues can pass. The recovery rate of the cells and/or tissues could also be improved by dilution with a physiological aqueous solution such as PBS and the like, or a chelate treatment. Furthermore, the recovery rate of the cells and/or tissues further increased by appropriately combining passage through filter, dilution and a chelate treatment. Based on these findings, further studies have been made, which resulted in the completion of the present invention.

That is, the present invention is as follows:

[1] A method of isolating cells or tissues from a culture preparation of the cells or tissues in a medium composition which enables culture of the cells or tissues in suspension, which comprises at least one step selected from the group consisting of the following (A), (B) and (C):
(A) passing the culture preparation through a filter having fine pores with a pore diameter of 5-500 μm, through which the cells or tissues can pass,
(B) adding a chelator to the culture preparation, and
(C) diluting the culture preparation with a physiological aqueous solution.
[2] The method of [1], comprising at least step (A), wherein the fine pores of the filter have a pore diameter of 20-100 μm.
[3] The method of [1] or [2], comprising at least step (A), wherein the culture preparation is passed through the filter plural times.
[4] The method of [1], comprising at least step (B), wherein the chelator is citric acid or a salt thereof.

[5] The method of [1] or [4], comprising at least step (B), wherein, after addition of the chelator, the mixture is stirred for not less than 10 min.
[6] The method of [1], comprising at least step (C), wherein the physiological aqueous solution is substantially free of calcium ion and magnesium ion.
[7] The method of [6], wherein the physiological aqueous solution is phosphate buffered saline.
[8] The method of any of [1]-[7], comprising all steps (A), (B) and (C).
[9] The method of [8], wherein the steps (A), (B) and (C) are performed in the order of (A), (B), (C).
[10] The method of any of [1]-[9], wherein the medium composition comprises deacylated gellan gum or a salt thereof.
[11] A reagent for isolating cells or tissues from a culture preparation of the cells or tissues in a medium composition which enables culture of the cells or tissues in suspension, which comprises at least one element selected from the group consisting of the following (A'), (B') and (C'):
(A') a filter having fine pores having a pore diameter of 5-500 μm,
(B') a chelator, and
(C') a physiological aqueous solution.
[12] The reagent of [11], comprising all of (A'), (B') and (C').
[13] The reagent of [11] or [12], further comprising deacylated gellan gum or a salt thereof.
(1') A pre-treatment method for recovering cells or tissues from a medium composition which enables culture of the cells or tissues in suspension, comprising a step of passing a medium composition comprising cells or tissues through a filter having fine pores with a pore diameter of 5-500 μm, through which the cells or tissues can pass.
(2') The method of (1'), comprising a step of adding a liquid medium.

Effect of the Invention

According to the present invention, animal and plant cells and/or tissues can be more efficiently recovered from an obtained culture preparation, after the animal and plant cells and/or tissues are cultured in a medium composition which enables culture of the cells or tissues in suspension.

According to the present invention, moreover, blood lineage cells (single cells) can be recovered easily, and analysis by a flow cytometry method can be performed.

DESCRIPTION OF EMBODIMENTS

The present invention is explained in more detail in the following.

The terms used in the present specification are defined as follows.

The medium composition to be used in the present invention is a medium composition containing a structure which enables culture of the cells or tissues in suspension. The medium composition enables culturing desired cells or a tissue containing the same while maintaining the suspending state. The medium composition can be prepared according to the descriptions of WO 2014/017513A1 and US 2014/0106348A1.

The cell in the present invention is a most basic unit constituting animals and plants, which has, as its elements, cytoplasm and various organelles inside the cellular membrane. In this case, the nucleus encapsulating the DNA may or may not be contained intracellularly. For example, the animal-derived cells in the present invention include reproductive cells such as spermatozoon, oocyte and the like, somatic cells constituting the living body, stem cells, progenitor cells, cancer cells separated from the living body, cells separated from the living body, which acquired immortalizing ability and is maintained stably in vitro (cell line), cells separated from the living body and applied with artificial genetic modification, cells separated from the living body wherein the nucleus is artificially exchanged, and the like. Examples of the somatic cells constituting the living body include, but are not limited to, fibroblast, bone marrow cells, B lymphocytes, T lymphocytes, neutrophils, red blood cells, platelets, macrophages, monocytes, osteocytes, bone marrow cells, pericytes, dendritic cells, keratinocytes, adipocytes, mesenchymal cells, epithelial cells, epidermal cells, endothelial cells, vascular endothelial cells, hepatocytes, chondrocytes, cumulus cells, nerve system cells, glial cells, neurons, oligodendrocytes, microglial, astrocytes, heart cells, esophagus cells, myocytes (e.g., smooth muscle cells or skeletal muscle cells), pancreatic beta cells, melanin cells, hematopoietic progenitor cells, mononuclear cells and the like. The somatic cells include cells collected from any tissue, for example, skin, kidney, spleen, adrenal gland, liver, lung, ovary, pancreas, uterus, stomach, colon, small intestine, large intestine, spleen, bladder, prostate, testis, thymus, muscle, connective tissue, bone, cartilage, blood vessel tissue, blood, heart, eye, brain, nerve tissue and the like. Stem cells are cells concurrently having an ability to replicate itself, and an ability to differentiate into other plural lineages. Examples thereof include, but are not limited to, embryonic stem cells (ES cell), embryonic tumor cells, embryonic reproductive stem cells, artificial pluripotent stem cells (iPS cell), neural stem cells, hematopoietic stem cells, mesenchymal stem cells, liver stem cells, pancreas stem cells, muscle stem cells, reproductive stem cells, intestinal stem cells, cancer stem cells, hair follicle stem cells and the like. Progenitor cells are cells on the way to differentiate from the aforementioned stem cell into a particular somatic cell or reproductive cell. Cancer cells are cells that are derived from a somatic cell and have acquired infinite proliferative capacity. Cell lines are cells that have acquired infinite proliferative capacity by an artificial operation in vitro, and examples thereof include, but are not limited to, CHO (Chinese hamster ovary cell line), HCT116, Huh7, HEK293 (human embryonic kidney cell), HeLa (human uterine cancer cell line), HepG2 (human liver cancer cell line), UT7/TPO (human leukemia cell line), MDCK, MDBK, BHK, C-33A, HT-29, AE-1, 3D9, Ns0/1, Jurkat, NIH3T3, PC12, S2, Sf9, Sf21, High Five (registered trademark), Vero and the like.

The plant-derived cell in the present invention also includes cells separated from each tissue of a plant body, as well as a protoplast obtained by artificially removing the cell wall from the cell.

The tissue in the present invention is a unit of a structure which is an assembly in a certain manner of cells having some kinds of different properties and functions, and examples of the animal tissue include epithelial tissue, connective tissue, muscular tissue, nerve tissue and the like. Examples of the plant tissue include meristem, epidermis tissue, assimilation tissue, mesophyll tissue, conductive tissue, mechanical tissue, parenchyma tissue, dedifferentiated cell cluster (callus) and the like.

When cells and/or tissues are cultured, the cells and/or tissues to be cultured can be selected freely from the cells and/or tissues described above and cultured. The cells and/or tissues can be directly recovered from an animal or plant body. The cells and/or tissues may be induced, grown or transformed from an animal or plant body by applying a particular treatment and then collected. In this case, the treatment may be in vivo or in vitro. Examples of the animal include fish, amphibian, reptiles, birds, pancrustacea, hexapoda, mammals and the like. Examples of the mammal include, but are not limited to, rat, mouse, rabbit, guinea pig, squirrel, hamster, vole, platypus, dolphin, whale, dog, cat, goat, bovine, horse, sheep, swine, elephant, common marmoset, squirrel monkey, Macaca mulatta, chimpanzee and human. The plant is not particularly limited as long as the collected cells and/or tissues can be applied to liquid culture. Examples thereof include, but are not limited to, plants producing crude drugs (e.g., saponin, alkaloids, berberine, scopolin, phytosterol etc.) (e.g., ginseng, periwinkle, henbane, coptis, belladonna etc.), plants producing dye or polysaccharide to be a starting material for cosmetic or food (e.g., anthocyanin, safflower dye, madder dye, saffron dye, flavones etc.) (e.g., blueberry, safflower, madder, saffron etc.), or plants producing a pharmaceutical drug substance and the like.

Suspending of cells and/or tissues in the present invention refers to a state where cells and/or tissues do not adhere to a culture container (non-adhesive). Furthermore, in the present invention, when the cells and/or tissues are proliferated, differentiated or maintained, the state where the cells and/or tissues are uniformly dispersed and suspended in the liquid medium composition in the absence of a pressure on or vibration of the liquid medium composition from the outside or shaking, rotating operation and the like in the composition is referred to as "static suspension", and cultivation of the cells and/or tissues in such condition is referred to as "static suspension culture". In the "static suspension", the period of suspending includes not less than 5 min (e.g., at least 5-60 min), not less than 1 hr (e.g., 1 hr-24 hr), not less than 24 hr (e.g., 1 day-21 days), not less than 48 hr, not less than 7 days etc., though the period is not limited thereto as long as the suspended state is maintained.

The medium composition to be used in the present invention permits static suspension of cells and/or tissues at least on one point in the temperature range (e.g., 0-40° C.) capable of maintaining or culturing cells or tissues. The medium composition to be used in the present invention permits static suspension of cells and/or tissues at least on one point in the temperature range of preferably 25-37° C., most preferably 37° C.

Whether static suspension is possible can be evaluated by, for example, uniformly dispersing the cells to be cultured in a medium composition to be evaluated at a concentration of $2 \times 10^4$ cells/ml, injecting 10 ml thereof in a 15 ml conical tube, standing the tube for at least not less than 5 min (e.g., not less than 1 hr, not less than 24 hr, not less than 48 hr, not less than 7 days) at 37° C., and observing whether the suspended state of the cells is maintained. When not less than 70% of the total cells are in a suspended state, it is concluded that the suspended state was maintained. Polystyrene beads (Size 500-600 μm, manufactured by Polysciences Inc.) may be used for evaluation instead of the cells A medium composition in the present invention is a composition containing a structure which enables culture of cells or tissues in suspension (preferably enables static suspension culture) and a medium.

The medium composition is preferably a composition permitting recovery of cells or tissues in an exchange treatment of the medium composition during culture and after completion of the culture.

The "structure which enables culture of cells or tissues in suspension" is formed from a particular compound and shows an effect of uniformly suspending cells and/or tissues. More particularly, it includes an assembly of polymer compounds via an ion, a three-dimensional network formed by polymer compounds and the like. It is known that polysaccharides form a microgel via a metal cation (e.g., JP-A-2004-129596), and the structure of the present invention also includes such microgel as one embodiment.

One embodiment of the assembly of polymer compounds via an ion is a film structure.

The size of the structure is preferably a size that passes a filter having a pore diameter of 0.2 μm to 200 μm when it is passed through a filter. The lower limit of the pore diameter is more preferably more than 1 μm and, in consideration of stable suspension of cells or tissues, it more preferably exceeds 5 μm. The upper limit of the pore diameter is more preferably not more than 100 μm and, in consideration of the size of the cells or tissues, it is more preferably not more than 70 μm.

The "particular compound" refers to a compound that forms, upon mixing with a liquid medium, an indeterminate structure which is uniformly dispersed in the liquid, substantially supports the cells and/or tissues without substantially increasing the viscosity of the liquid, and shows an effect of preventing sediment thereof. The "without substantially increasing the viscosity of the liquid" means that the viscosity of the liquid does not exceed 8 mPa·s. In this case, the viscosity of the liquid (that is, the viscosity of the medium composition in the present invention) is not more than 8 mPa·s, preferably not more than 4 mPa·s, more preferably not more than 2 mPa·s, at 37° C. Furthermore, the chemical structure, molecular weight, property etc. of the particular compound are not limited as long as it forms the structure in a liquid medium, and shows an effect of uniformly suspending (preferably statically suspending) the cells and/or tissues without substantially increasing the viscosity of the liquid.

The viscosity of the liquid containing the structure can be measured, for example, by the method described in the below-mentioned Examples. Specifically, it can be measured under 37° C. conditions and using an E-type viscosity meter (manufactured by Toki Sangyo Co., Ltd., TV-22 type viscosity meter, model: TVE-22 L, corn roter: standard roter 1°34'×R24, rotating speed 100 rpm).

Examples of the "particular compound" include, but are not limited to, polymer compounds, preferably a polymer compound having an anionic functional group.

As the anionic functional group, a carboxy group, sulfonic group, phosphate group and a salt thereof can be mentioned, with preference given to carboxy group or a salt thereof.

As the polymer compound to be used in the present invention, one constituted of one or more kinds selected from the group consisting of the aforementioned anionic functional groups can be used.

Specific preferable examples of the polymer compound to be used in the present invention include, but are not limited to, polysaccharides wherein not less than 10 monosaccharides (e.g., triose, tetrose, pentose, hexsauce, heptose etc.) are polymerized, more preferably, acidic polysaccharides having an anionic functional group. The acidic polysaccharide here is not particularly limited as long as it has an anionic functional group in the structure thereof, and includes, for example, polysaccharides having a uronic acid (e.g., glucuronic acid, iduronic acid, galacturonic acid, mannuronic acid), polysaccharides having sulfate or phosphate in a part of the structure thereof, and polysaccharides having the both structures, and includes not only naturally-obtained polysaccharides but also polysaccharides produced by microorganisms, polysaccharides produced by genetic engineering, and polysaccharides artificially synthesized using an enzyme. More specifically, examples thereof include polymer compounds composed of one or two of more kinds selected from the group consisting of hyaluronic acid, gellan gum, deacylated gellan gum (DAG), rhamsan gum, diutan gum, xanthan gum, carageenan, xanthan gum, hexuronic acid, fucoidan, pectin, pectic acid, pectinic acid, heparan sulfate, heparin, heparitin sulfate, keratosulfate, chondroitin sulfate, dermatan sulfate, rhamnan sulfate and a salt thereof. Polysaccharides are preferably hyaluronic acid, DAG, diutan gum, xanthan gum, carageenan or a salt thereof, most preferably DAG since use thereof at a low concentration can suspend cells or tissues and in consideration of easy recovery of the cells or tissues.

Examples of the salt here include alkali metal salts such as lithium, sodium, potassium; alkaline earth metal salts such as calcium, barium, magnesium; salts such as aluminum, zinc, copper, iron and the like; ammonium salt; quarternary ammonium salts such as tetraethylammonium, tetrabutylammonium, methyltributylammonium, cetyl trimethylammonium, benzylmethylhexyldecylammonium, choline and the like; salts with organic amines such as pyridine, triethylamine, diisopropylamine, ethanolamine, diolamine, tromethamine, meglumine, procaine, chloroprocaine and the like; salts with amino acid such as glycine, alanine, valine and the like; and the like.

The weight average molecular weight of these polymer compounds or polysaccharides is preferably 10,000 to 50,000,000, more preferably 100,000 to 20,000,000, still more preferably 1,000,000 to 10,000,000. For example, the molecular weight can be measured based on pullulan by gel penetration chromatography (GPC).

Furthermore, phosphorylated DAG can also be used. The phosphorylation can be performed by a known method.

In the present invention, plural kinds (preferably two kinds) of the above-mentioned polysaccharides can be used in combination. The kind of the combination of the polysaccharides is not particularly limited as long as the aforementioned structure is formed in a liquid medium, and the cells and/or tissues can be uniformly suspended (preferably statically suspended) without substantially increasing the viscosity of the liquid. Preferably, the combination includes at least DAG or a salt thereof. That is, a preferable combination of polysaccharides comprises DAG or a salt thereof, and a polysaccharide other than DAG and a salt thereof (e.g., xanthan gum, alginic acid, carageenan, diutan gum, methylcellulose, locust bean gum or a salt thereof). Examples of specific combination of polysaccharides include, but are not limited to, DAG and rhamsan gum, DAG and diutan gum, DAG and xanthan gum, DAG and carageenan, DAG and xanthan gum, DAG and locust bean gum, DAG and κ-carageenan, DAG and sodium alginate, DAG and methylcellulose and the like.

More Specific preferable examples of the "particular compound" include hyaluronic acid, deacylated gellan gum, diutan gum, carageenan and xanthan gum and a salt thereof. Most preferable examples include deacylated gellan gum and a salt thereof, since the viscosity of the medium composition can be made low and the cells or tissues can be easily recovered.

The deacylated gellan gum in the present invention is a linear polymer polysaccharide containing 4 molecules of sugars of 1-3 bonded glucose, 1-4 bonded glucuronic acid, 1-4 bonded glucose and 1-4 bonded rhamnose as the constituent unit, which is a polysaccharide of the following formula (I) wherein $R_1$, $R_2$ are each a hydrogen atom, and n is an integer of two or more. $R_1$ may contain a glyceryl group, $R_2$ may contain an acetyl group, and the content of the acetyl group and glyceryl group is preferably not more than 10%, more preferably not more than 1%.

The aforementioned structure takes various forms depending on the particular compound. In the case of deacylated gellan gum, it uptakes metal cations (e.g., calcium ion) in a liquid medium when mixed with the liquid medium, forms an indeterminate structure via the metal cation, and enables suspending the cells and/or tissues. The viscosity of the medium composition prepared from deacylated gellan gum is not more than 8 mPa·s, preferably not more than 4 mPa·s, and more preferably not more than 2 mPa·s in consideration of easy recovery of the cells or tissues.

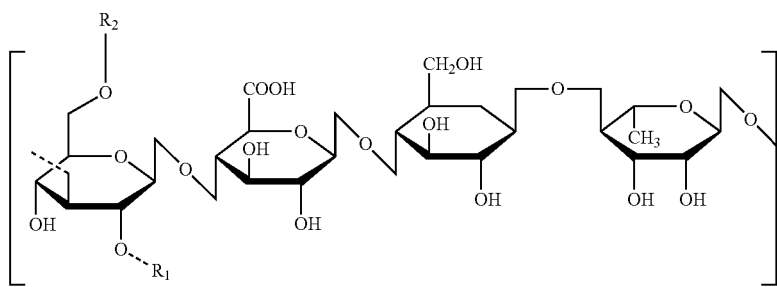

(I)

The "particular compound" can be obtained by a chemical synthesis method. When the compound is a naturally-occurring substance, it is preferably obtained from various plants, various animals, various microorganisms containing the compound by extraction, separation and purification by conventional techniques. For extraction, the compound can be extracted efficiently by using water and supercritical gas. For example, as a production method of gellan gum, a producing microorganism is cultured in a fermentation medium, a mucosal product produced outside fungus body is recovered by a general purification method and, after the steps of drying, pulverizing and the like, powderized. When it is deacylated gellan gum, an alkali treatment is applied when a mucous product is recovered, the glyceryl group and the acetyl group bonded to 1-3 bonded glucose residue are deacylated and recovered. Examples of the purification method include liquid-liquid extraction, fractional precipitation, crystallization, various kinds of ion exchange chromatography, gel filtration chromatography using Sephadex LH-20 and the like, adsorption chromatography using activated carbon, silica gel and the like, adsorption and desorption treatment of active substance by thin layer chromatography, high performance liquid chromatography using reversed-phase column and the like, and impurity can be removed and the compound can be purified by using them singly or in combination in any order, or repeatedly. Examples of the gellan gum-producing microorganism include, but are not limited to, Sphingomonas elodea and microorganisms obtained by modifying the gene of Sphingomonas elodea.

In the case of deacylated gellan gum, commercially available products, for example, "KELCOGEL (registered trade mark of CP Kelco) CG-LA" manufactured by SANSHO Co., Ltd., "KELCOGEL (registered trade mark of CP Kelco)" manufactured by San-Ei Gen F.F.I., Inc. and the like can be used. As a native gellan gum, "KELCOGEL (registered trade mark of CP Kelco) HT" manufactured by San-Ei Gen F.F.I., Inc. and the like can be used.

The concentration of the particular compound in a medium is 0.0005% to 1.0% (W/V), preferably 0.001% to 0.4% (W/V), more preferably 0.005% to 0.1% (W/V), still more preferably 0.005% to 0.05% (W/V). For example, in the case of deacylated gellan gum, it is added to a medium at 0.001% to 1.0% (W/V), preferably 0.003% to 0.5% (W/V), more preferably 0.005% to 0.3% (W/V) (or 0.005% to 0.1% (W/V)), more preferably 0.01% to 0.05% (W/V), most preferably, 0.01% to 0.03% (W/V) (or 0.01% to 0.02% (W/V)). In the case of xanthan gum, it is added to a medium at 0.001% to 5.0% (W/V), preferably 0.01% to 1.0% (W/V), more preferably 0.05% to 0.5% (W/V), most preferably 0.1% to 0.2% (W/V). In the case of a κ-carageenan and locust bean gum mixture, it is added to a medium at 0.001% to 5.0% (W/V), preferably 0.005% to 1.0% (W/V), more preferably 0.01% to 0.1% (W/V), most preferably 0.03% to 0.05% (W/V). In the case of a native gellan gum, it is added to a medium at 0.05% to 1.0% (W/V), preferably 0.05% to 0.1% (W/V).

When plural kinds (preferably two kinds) of the above-mentioned polysaccharides are used in combination, the concentration of the polysaccharides can be appropriately set within the range where the polysaccharides can form the aforementioned structure in a liquid medium, and enables suspending (preferably statically suspending) the cells and/or tissues uniformly without substantially increasing the viscosity of the liquid. For example, when a combination of DAG or a salt thereof and a polysaccharide other than DAG and a salt thereof is used, the concentration of DAG or a salt thereof is, for example, 0.005-0.02% (W/V), preferably 0.01-0.02% (W/V), and the concentration of the polysaccharide other than DAG and a salt thereof is, for example, 0.0001-0.4% (W/V), preferably 0.005-0.4% (W/V), more preferably 0.1-0.4% (W/V). Specific examples of the combination of the concentration range include the following.

DAG or a salt thereof: 0.005-0.02% (preferably 0.01-0.02%) (W/V)

polysaccharide other than DAG
xanthan gum: 0.1-0.4% (W/V)
sodium alginate: 0.0001-0.4% (W/V) (preferably 0.1-0.4% (W/V))
native gellan gum: 0.0001-0.4% (W/V)
locust bean gum: 0.1-0.4% (W/V)
methylcellulose: 0.1-0.4% (W/V) (preferably 0.2-0.4% (W/V))
carageenan: 0.05-0.1% (W/V)
diutan gum: 0.05-0.1% (W/V)

The concentration can be calculated by the following formula.

$$\text{Concentration } [\% (W/V)] = \text{weight (g) of particular compound/volume (ml) of medium composition} \times 100$$

The aforementioned compound can also be further converted to a different derivative by a chemical synthesis method, and the thus-obtained derivative can also be used effectively in the present invention. Specifically, in the case of deacylated gellan gum, a derivative of a compound represented by the formula (I) wherein a hydroxyl group for $R_1$ and/or $R_2$ is substituted by $C_{1-3}$ alkoxy group, $C_{1-3}$ alkylsulfonyl group, a monosaccharide residue such as glucose, fructose and the like, oligosaccharide residue such as sucrose, lactose and the like, or amino acid residue such as glycine, arginine and the like can also be used in the present invention. In addition, the compound can also be crosslinked using a crosslinker such as 1-ethyl-3-(3-dimethylaminopropyl)carbodiimide (EDC) and the like.

The particular compound or a salt thereof to be used in the present invention can be present in any crystal form depending on the production conditions, and can be present as any hydrate. Such crystal form, hydrate and mixtures thereof are also encompassed in the scope of the present invention. In addition, they may be present as a solvate containing an organic solvent such as acetone, ethanol, tetrahydrofuran and the like. Such forms are all encompassed in the scope of the present invention.

The particular compound to be used in the present invention may be present in the form of tautomer, geometric isomer or tautomer, or a mixture of geometric isomers, or mixtures thereof formed by isomerization in the ring or outside the ring. When the compound to be used in the present invention has an asymmetric center, irrespective of whether the compound is formed by isomerization, it may be present in the form of a resolved optical isomer or a mixture containing same at any ratio.

The medium composition in the present invention contains metal cations, for example, divalent metal cations (calcium ion, magnesium ion, zinc ion, iron ion and copper ion etc.), preferably calcium ion. Two or more kinds of metal ions can be used in combination, for example, calcium ion and magnesium ion, calcium ion and zinc ion, calcium ion and ferrous ion, and calcium ion and copper ion. Those of ordinary skill in the art can appropriately determine the combination. In one embodiment, when metal cations (e.g., calcium ion) are contained, polymer compounds (e.g., polysaccharides) gather via the metal cation; the polymer compounds (e.g., polysaccharides) form a three dimensional network; or the polymer compounds (e.g., polysaccharides) form a microgel via the metal cation, whereby the structure which enables suspending the cells or tissues can be formed. The metal ion concentration is, but is not limited to, 0.1 mM-300 mM, preferably 0.5 mM-100 mM. The metal ion may be mixed with a medium, or a salt solution may be separately prepared and added to the medium.

The medium composition to be used in the present invention may contain the below-mentioned extracellular matrix, adhesion molecule and the like.

The present invention also includes a culture method for proliferating cells or tissues by using the above-mentioned medium composition, a method of recovering the obtained cells or tissues by, for example, filtration, centrifugation or magnetic separation, and a production method of a sphere by using the medium composition.

The structure composed of the particular compound to be used in the present invention exerts an effect of suspending (preferably effect of statically suspending) cells and/or tissues in a liquid containing the structure of the particular compound, when the cells and/or tissues are cultured in vitro. By the suspension effect, a more increased amount of the cells and/or tissues per a given volume can be cultured as compared to a monolayer culture. When rotation or shaking operation is accompanied in a conventional suspension culture method, the proliferation rate and recovery rate of the cells and/or tissues may become low, or the function of the cells may be impaired since a shear force acts on the cells and/or tissues. Using the medium composition, which contains the structure composed of the particular compound, can uniformly disperse the cells and/or tissues without an operation such as shaking and the like, and can obtain the object cells and/or tissues easily in a large amount without loss of the cell function. In addition, when cells and/or tissues are cultured in suspension in a conventional medium containing a gel substrate, observation and recovery of the cells and/or tissues are sometimes difficult, and the function thereof is sometimes impaired during recovery. However, using the medium composition containing the structure composed of the particular compound, the cells and/or tissues can be cultured in suspension, observed without impairing the function thereof, and recovered. In addition, a conventional medium containing a gel substrate sometimes shows high viscosity that makes it difficult to exchange the medium. However, since the medium composition containing the structure composed of the particular compound has low viscosity, it can be exchanged easily with a pipette, pump and the like.

The human-derived cells and/or tissues cultured by the present invention can be transplanted for a treatment object to patients having a disease or disorder. In this case, treatment target disease, the kind of disorder, a pre-treatment method and a cell transplantation method are appropriately selected by those of ordinary skill in the art. The engraftment of the transplanted cells in the recipient, recovery from the disease or disorder, the presence or absence of side effects associated with transplantation, and treatment effect are appropriately examined and judged by general methods for transplantation therapy.

Since cells and/or tissues are grown efficiently, moreover, a medium composition in the present invention can be used as a reagent for the study of cells. For example, when a factor controlling the differentiation and proliferation of cells and tissues is to be elucidated, cells and the object factor are cocultured, and the number and kind of cells, and changes in the cell surface differentiation marker and expressed gene are analyzed. In this case, using the medium composition to be used in the present invention, the number of the analysis target cells can be efficiently amplified, and efficiently recovered as well. When the object factor is elucidated, the culture conditions, culture apparatus, the kind of medium, the kind of the compound to be used in the present invention, the content of the particular compound, the kind of the additive, the content of the additive, culture period, culture temperature and the like are appropriately selected by those of ordinary skill in the art from the range described in the present specification. The cells that were proliferated or emerged by culture can be observed using a standard microscope in the pertinent field. In this case, cultured cells may be stained with a specific antibody. The expressed gene that has changed due to the object factor can be detected by extracting the RNA (ribonucleic acid) from the cultured cells and performing Northern Blotting, RT-PCR and the like. In addition, a cell surface differentiation marker can be detected by ELISA and flow cytometry using a specific antibody, and the effect of the object factor on the differentiation and proliferation can be observed.

When cells and/or tissues are cultured by the culture method to be used in the present invention, culture tools generally used for cell culture such as schale, flask, plastic bag, Teflon (registered trade mark) bag, dish, schale, dish for tissue culture, multidish, microplate, microwell plate, multiplate, multiwell plate, chamber slide, tube, tray, culture bag, roller bottle and the like can be used for cultivation. While the materials of these culture tools are not particularly limited, for example, plastic and the like such as glass, polyvinyl chloride, cellulose-based polymer, polystyrene, polymethylmethacrylate, polycarbonate, polysulfone, polyurethane, polyester, polyamide, polystyrene, polypropylene and the like can be mentioned. Moreover, these plastics may be applied with various surface treatments (e.g., plasma treatment, corona treatment etc.). Furthermore, these culture tools may be coated in advance with an extracellular matrix, a cell adhesion molecule and the like. Examples of the coating material include collagen I to XIX, fibronectin, vitronectin, laminin-1 to 12, nitrogen, tenascin, thrombospondin, von Willebrand factor, osteopontin, fibrinogen, various elastins, various proteoglycans, various cadherins, desmocolin, desmoglein, various integrins, E-selectin, P-selectin, L-selectin, immunoglobulin, hyaluronic acid, superfamily, Matrigel, poly-D-lysine, poly-L-lysine, chitin, chitosan, sepharose, alginic acid gel, hydrogel, cleavage fragments thereof and the like. These coating materials having an amino acid sequence artificially altered by gene recombination techniques can also be used. A coating material for inhibiting adhesion of the cells and/or tissues to culture tools can also be used. Examples of the coating material include, but are not limited to, silicon, poly(2-hydroxymethylmethacrylate), poly(2-methacryloyloxyethylphosphoryl choline) and the like.

The cells and/or tissues can also be cultured by automatically conducting cell seeding, medium exchange, cell image obtainment, and recovery of cultured cells, under a mechanical control and under a closed environment while controlling pH, temperature, oxygen concentration and the like and using a bioreactor and an automatic incubator capable of high density culture. As a method for supplying a new medium and feeding the required substances to the cells and/or tissues during the culture using such apparatuses, fed-batch culture, continuous culture and perfusion culture are available, and all these methods can be used for the culture method in the present invention.

When cells and/or tissues are cultured using the particular compound of the present invention, a medium composition can be prepared by mixing a medium used for culturing cells and/or tissues, and the particular compound.

Examples of the medium include Dulbecco's Modified Eagle's Medium (DMEM), hamF12 medium (Ham's Nutrient Mixture F12), DMEM/F12 medium, McCoy's 5A medium, Eagle MEM medium (Eagle's Minimum Essential Medium; EMEM), αMEM medium (alpha Modified Eagle's Minimum Essential Medium; αMEM), MEM medium (Minimum Essential Medium), RPMI1640 medium, Iscove's Modified Dulbecco's Medium (IMDM), MCDB131 medium, William medium E, IPL41 medium, Fischer's medium, StemPro34 (manufactured by Invitrogen), X-VIVO 10 (manufactured by Cambrex Corporation), X-VIVO 15 (manufactured by Cambrex Corporation), HPGM (manufactured by Cambrex Corporation), StemSpan H3000 (manufactured by STEMCELL Technologies), Stem- SpanSFEM (manufactured by STEMCELL Technologies), StemlineII (manufactured by Sigma Aldrich), QBSF-60 (manufactured by Qualitybiological), StemPro hESC SFM (manufactured by Invitrogen), mTeSR1 or 2 medium (manufactured by STEMCELL Technologies), Sf-900II (manufactured by Invitrogen), Opti-Pro (manufactured by Invitrogen), and the like.

When the cells and/or tissues are derived from a plant, a medium obtained by adding auxins and, where necessary, a plant growth control substance (plant hormone) such as cytokinins and the like at a suitable concentration to a basic medium such as Murashige Skoog (MS) medium, Linsmaier Skoog (LS) medium, White medium, Gamborg's B5 medium, niche medium, hela medium, Morel medium and the like generally used for culture of plant tissues, or a modified medium wherein these medium components are modified to an optimal concentration (e.g., ammonia nitrogen at a half concentration etc.) can be mentioned as the medium. These media can be further supplemented, where necessary, with casein degrading enzyme, corn steep liquor, vitamins and the like. Examples of the auxins include, but are not limited to, 3-indoleacetic acid (IAA), 3-indolebutyric acid (IBA), 1-naphthaleneacetic acid (NAA), 2,4-dichlorophenoxyacetic acid (2,4-D) and the like. For example, auxins can be added to a medium at a concentration of about 0.1-about 10 ppm. Examples of the cytokinins include, but are not limited to, kinetin, benzyladenine (BA), zeatin and the like. For example, cytokinins can be added to a medium at a concentration of about 0.1-about 10 ppm.

Those of ordinary skill in the art can freely add, according to the object, sodium, potassium, calcium, magnesium, phosphorus, chlorine, various amino acids, various vitamins, antibiotic, serum, fatty acid, sugar and the like to the above-mentioned medium. For culture of animal-derived cells and/or tissues, those of ordinary skill in the art can also add, according to the object, one or more kinds of other chemical components and biogenic substances in combination. Examples of the components to be added to a medium for animal-derived cells and/or tissues include fetal bovine serum, human serum, horse serum, insulin, transferrin, lactoferrin, cholesterol, ethanolamine, sodium selenite, monothioglycerol, 2-mercaptoethanol, bovine serum albumin, sodium pyruvate, polyethylene glycol, various vitamins, various amino acids, agar, agarose, collagen, methylcellulose, various cytokines, various hormones, various proliferation factors, various extracellular matrices, various cell adhesion molecules and the like. Examples of the cytokine to be added to a medium include, but are not limited to, interleukin-1 (IL-1), interleukin-2 (IL-2), interleukin-3 (IL-3), interleukin-4 (IL-4), interleukin-5 (IL-5), interleukin-6 (IL-6), interleukin-7 (IL-7), interleukin-8 (IL-8), interleukin-9 (IL-9), interleukin-10 (IL-10), interleukin-11 (IL-11), interleukin-12 (IL-12), interleukin-13 (IL-13), interleukin-14 (IL-14), interleukin-15 (IL-15), interleukin-18 (IL-18), interleukin-21 (IL-21), interferon-$\alpha$ (IFN-$\alpha$), interferon-$\beta$ (IFN-$\beta$), interferon-$\gamma$ (IFN-$\gamma$), granulocyte colony stimulating factor (G-CSF), monocyte colony stimulating factor (M-CSF), granulocyte-macrophage colony stimulating factor (GM-CSF), stem cell factor (SCF), flk2/flt3 ligand (FL), leukemia cell inhibitory factor (LIF), oncostatin M (OM), erythropoietin (EPO), thrombopoietin (TPO) and the like.

Examples of the hormone to be added to a medium include, but are not limited to, melatonin, serotonin, thyroxine, triiodothyronine, epinephrine, norepinephrine, dopamine, anti-Mullerian hormone, adiponectin, adrenocorticotropic hormone, angiotensinogen and angiotensin, antidiuretic hormone, atrial natriuretic peptide, calcitonin, cholecystokinin, corticotropin release hormone, erythropoietin, follicle stimulating hormone, gastrin, ghrelin, glucagon, gonadotropin release hormone, growth hormone release hormone, human chorionic gonadotropin, human placental lactogen, growth hormone, inhibin, insulin, insulin-like growth factor, leptin, luteinizing hormone, melanocyte stimulating hormone, oxytocin, parathyroid hormone, prolactin, secretin, somatostatin, thrombopoietin, thyroid-stimulating hormone, thyrotropin releasing hormone, cortisol, aldosterone, testosterone, dehydroepiandrosterone, androstenedione, dihydrotestosterone, estradiol, estrone, estriol, progesterone, calcitriol, calcidiol, prostaglandin, leukotriene, prostacyclin, thromboxane, prolactin releasing hormone, lipotropin, brain natriuretic peptide, neuropeptide Y, histamine, endothelin, pancreas polypeptide, rennin and enkephalin.

Examples of the growth factor to be added to a medium include, but are not limited to, transforming growth factor-$\alpha$ (TGF-$\alpha$), transforming growth factor-$\beta$ (TGF-$\beta$), macrophage inflammatory protein-1$\alpha$ (MIP-1$\alpha$), epithelial cell growth factor (EGF), fibroblast growth factor-1, 2, 3, 4, 5, 6, 7, 8 or 9 (FGF-1, 2, 3, 4, 5, 6, 7, 8, 9), nerve cell growth factor (NGF) hepatocyte growth factor (HGF), leukemia inhibitory factor (LIF), protease nexin I, protease nexin II, platelet-derived growth factor (PDGF), choline vasoactive differentiation factor (CDF), chemokine, Notch ligand (Delta1 and the like), Wnt protein, angiopoietin-like protein 2, 3, 5 or 7 (Angpt2, 3, 5, 7), insulin like growth factor (IGF), insulin-like growth factor binding protein-1 (IGFBP), Pleiotrophin and the like.

In addition, these cytokines and growth factors having amino acid sequences artificially altered by gene recombinant techniques can also be added. Examples thereof include IL-6/soluble IL-6 receptor complex, Hyper IL-6 (fusion protein of IL-6 and soluble IL-6 receptor) and the like.

Examples of the various extracellular matrices and various cell adhesion molecules include collagen I to XIX, fibronectin, vitronectin, laminin-1 to 12, nitrogen, tenascin, thrombospondin, von Willebrand factor, osteopontin, fibrinogen, various elastins, various proteoglycans, various cadherins, desmocolin, desmoglein, various integrins, E-selectin, P-selectin, L-selectin, immunoglobulin superfamily, Matrigel, poly-D-lysine, poly-L-lysine, chitin, chitosan, sepharose, hyaluronic acid, alginate gel, various hydrogels, cleavage fragments thereof and the like.

Examples of the antibiotic to be added to a medium include Sulfonamides and preparations, penicillin, phenethicillin, methicillin, oxacillin, cloxacillin, dicloxacillin, flucloxacillin, nafcillin, ampicillin, penicillin, amoxicillin, ciclacillin, carbenicillin, ticarcillin, piperacillin, azlocillin, mezlocillin, mecillinam, andinocillin, cephalosporin and a derivative thereof, oxolinic acid, amifloxacin, temafloxacin, nalidixic acid, Piromidic acid, ciprofloxacin, cinoxacin, norfloxacin, perfloxacin, Rosaxacin, ofloxacin, enoxacin, pipemidic acid, sulbactam, clavulanic acid, $\beta$-bromopenisillanic acid, $\beta$-chloropenisillanic acid, 6-acetylmethylene-penisillanic acid, cephoxazole, sultampicillin, adinoshirin and sulbactam formaldehyde hudrate ester, tazobactam, aztreonam, sulfazethin, isosulfazethin, norcardicin, m-carboxyphenyl, phenylacetamidophosphonic acid methyl, Chlortetracycline, oxytetracycline, tetracycline, demeclocycline, doxycycline, methacycline, and minocycline.

In a preferable embodiment, the medium contains metal cations, for example, divalent metal cations (calcium ion, magnesium ion, zinc ion, iron ion and copper ion etc.), preferably calcium ion. Calcium ion is contained in 0.1-10 mM, preferably 0.5-3.0 mM. When metal cations are contained, the polymer compounds having an anionic functional group gather via the metal cation; the polymer compounds having an anionic functional group form a three dimensional network; or the polymer compounds having an anionic functional group form a microgel via the metal cation, whereby the structure which enables culture of cells or tissues in suspension can be formed.

When the particular compound in the present invention is added to the above-mentioned medium, the particular compound is dissolved or dispersed in an appropriate solvent when in use (this is used as a medium additive). Thereafter, the medium additives can be added to a medium such that the concentration of the particular compound in the medium is, as described in detail above, a concentration at which the cells and/or tissues can be uniformly suspended (preferably statically suspended) without substantially increasing the viscosity of the liquid medium, for example, 0.0005% to 1.0% (W/V), preferably 0.001% to 0.4% (W/V), more preferably 0.005% to 0.1% (W/V), further preferably 0.005% to 0.05% (W/V). For example, in the case of deacylated gellan gum, it is added to a medium at 0.001% to 1.0% (W/V), preferably 0.003% to 0.5% (W/V), more preferably 0.005% to 0.3% (W/V) (or 0.005% to 0.1% (W/V)), most preferably 0.01% to 0.05% (W/V) (or 0.01% to 0.03% (W/V)). In another aspect, in the case of deacylated gellan gum, it is added to a medium at 0.0005% to 1.0% (W/V), preferably 0.001% to 0.5% (W/V), more preferably 0.003% to 0.1% (W/V), most preferably 0.005% to 0.03% (W/V). In the case of xanthan gum, it is added to a medium at 0.001% to 5.0% (W/V), preferably 0.01% to 1.0% (W/V), more preferably 0.05% to 0.5% (W/V), most preferably 0.1% to 0.2% (W/V). In the case of a mixture of κ-carageenan and locust bean gum, it is added to a medium at 0.001% to 5.0% (W/V), preferably 0.005% to 1.0% (W/V), more preferably 0.01% to 0.1%, most preferably 0.03% to 0.05% (W/V), in the total of the both compounds. In the case of a mixture of deacylated gellan gum and diutan gum, it is added to a medium at 0.001% to 1.0% (W/V), most preferably 0.005% to 0.01% (W/V), in the total of the both compounds. In the case of a mixture of deacylated gellan gum and methylcellulose, it is added to a medium at 0.001% to 1.0% (W/V), most preferably 0.005% to 0.2% (W/V), in the total of the both compounds. In the case of a mixture of deacylated gellan gum and locust bean gum, it is added to a medium at 0.001% to 1.0% (W/V), most preferably 0.01% to 0.1% (W/V), in the total of the both compounds. In the case of a mixture of deacylated gellan gum and sodium alginate, it is added to a medium at 0.001% to 1.0% (W/V), most preferably 0.01% to 0.1% (W/V), in the total of the both compounds. In the case of a mixture of deacylated gellan gum and xanthan gum, it is added to a medium at 0.001% to 1.0% (W/V), most preferably 0.01% to 0.1% (W/V), in the total of the both compounds. In the case of a mixture of deacylated gellan gum and κ-carageenan, it is added to a medium at 0.001% to 1.0% (W/V), most preferably 0.01% to 0.1% (W/V), in the total of the both compounds. The concentration can be calculated by the following formula.

Concentration [% (W/V)]=weight (g) of particular compound/volume (ml) of medium composition×100

Here, examples of appropriate solvent used for the medium additive include, but are not limited to, aqueous solvents such as water, dimethyl sulfoxide (DMSO), various alcohols (e.g., methanol, ethanol, butanol, propanol, glycerol, propylene glycol, butyleneglycol and the like), and the like. In this case, the concentration of the particular compound is 0.001% to 5.0% (W/V), preferably 0.01% to 1.0% (W/V), more preferably 0.1% to 0.6% (W/V). It is also possible to further add an additive to enhance the effect of the particular compound, or lower the concentration when in use. As an example of such additive, one or more kinds of polysaccharides including guargum, alginic acid propylene glycol ester, locust bean gum, gum arabic, tara gum, tamarind gum, methylcellulose, carboxymethylcellulose, agarose, tamarind seed gum, pullulan and the like can be mixed. It is also possible to immobilize the particular compound on the surface of a carrier or carry the particular compound inside a carrier during culture. The particular compound may be in the form of a formulated solid such as powder, tablet, pill, capsule, granule, or a liquid such as a solution obtained by dissolving in an appropriate solvent using a solubilizer or a suspension, or may be bonded to a substrate or a single substance. Examples of the additive used for formulating include preservatives such as p-oxybenzoic acid esters and the like; excipients such as lactose, glucose, sucrose, mannit and the like; lubricants such as magnesium stearate, talc and the like; binders such as poly(vinyl alcohol), hydroxypropylcellulose, gelatin and the like; surfactants such as fatty acid ester and the like; plasticizers such as glycerol and the like; and the like. These additives are not limited to those mentioned above, and can be selected freely as long as they are utilizable for those of ordinary skill in the art. In addition, the particular compound in the present invention may be sterilized as necessary. The sterilization method is not particularly limited, and, for example, radiation sterilization, ethylene oxide gas sterilization, autoclave sterilization, filter sterilization and the like can be mentioned. When filter sterilization (hereinafter sometimes to be referred to as filtration sterilization) is to be performed, the material of the filter part is not particularly limited and, for example, glass fiber, nylon, PES (polyethersulfone), hydrophilic PVDF (polyvinylidene fluoride), cellulose mixed ester, celluloseacetate, polytetrafluoroethylene and the like can be mentioned. While the size of the pore in the filter is not particularly limited, it is preferably 0.1 μm to 10 μm, more preferably 0.1 μm to 1 μm, most preferably 0.1 μm to 0.5 μm. These sterilization treatments can be applied regardless of whether the particular compound is in a solid state or in a solution state.

A solution or dispersion of a particular compound obtained by the above-mentioned preparation is added to a liquid medium, whereby the above-mentioned structure is formed in the liquid medium and the medium composition can be obtained. Since a medium generally contains metal ions at a concentration sufficient for polymer compounds to gather via the ions or for the polymer compounds to form a three dimensional network, the medium composition can be obtained by simply adding a solution or dispersion of a particular compound to a liquid medium. Alternatively, a medium may be added to a medium additive (solution or dispersion of particular compound). Furthermore, the medium composition can also be prepared by mixing a particular compound and a medium component in an aqueous solvent (e.g., water including ion exchanged water, ultrapure water and the like). Examples of the embodiment of mixing include, but are not limited to, (1) mixing a liquid medium and a medium additive (solution), (2) mixing a liquid medium and the above-mentioned polymer compound (solid such as powder and the like), (3) mixing a medium additive (solution) and a powder medium, (4) mixing a powder medium and the above-mentioned polymer compound (solid such as powder and the like) and an aqueous solvent, and the like. To prevent distribution of a particular compound in a medium composition from being non-uniform, the embodiment of (1) or (4) or (1) or (3) is preferable.

When a particular compound is dissolved in a solvent (e.g., aqueous solvent such as water, liquid medium and the like), or a particular compound and a powder medium are dissolved in a solvent, it is preferable to heat the mixture to promote dissolution. Examples of the heat temperature include 80° C.-130° C., preferably 100° C.-125° C. (e.g., 121° C.) at which heating sterilization is performed. After heating, the obtained solution of the particular compound is cooled to room temperature. By adding the aforementioned metal ions (e.g., divalent metal ions such as calcium ion and the like) to the solution (e.g., adding the solution to liquid medium), the above-mentioned structure constituted of the particular compound can be formed. Alternatively, the above-mentioned structure constituted of the particular compound can also be formed by dissolving a particular compound in a solvent (e.g., aqueous solvent such as water, liquid medium and the like) containing the aforementioned metal ions (e.g., divalent metal ions such as calcium ion and the like), heating (e.g., 80° C.-130° C., preferably 100° C.-125° C. (e.g., 121° C.)), and cooling the obtained solution to room temperature.

Examples of the production method of the medium composition to be used in the present invention are shown below, which are not to be construed as limitative. A particular compound is added to ion exchange water or ultrapure water. Then, the mixture is stirred at a temperature at which the particular compound can be dissolved (e.g., 5-60° C., preferably 5-40° C., more preferably 10-30° C.) to allow for dissolution to a transparent state.

After dissolving, the mixture is allowed to cool with stirring as necessary, and sterilized (e.g., autoclave sterilization at 121° C. for 20 min, filter filtration). The aforementioned sterilized aqueous solution is added with stirring (e.g., homomixer etc.) to a given medium to be used for static culture to uniformly mix the solution with the medium. The mixing method of the aqueous solution and the medium is not particularly limited, and may be manual mixing such as pipetting etc., or mixing with an instrument such as magnetic stirrer, mechanical stirrer, homomixer and homogenizer. Furthermore, the medium composition may be filtrated through a filter after mixing. The size of the pore of the filter to be used for the filtration treatment is 5 μm to 100 μm, preferably 5 μm to 70 μm, more preferably 10 μm to 70 μm.

Alternatively, a powder medium and the above-mentioned polymer compound (solid such as powder and the like) are mixed with an aqueous solvent, and the mixture is heated at the above-mentioned temperature to give a medium composition to be used in the present invention.

For example, when deacylated gellan gum is prepared, deacylated gellan gum is added to ion exchange water or ultrapure water at 0.1% to 1% (W/V), preferably 0.2% to 0.5% (W/V), more preferably 0.3% to 0.4% (W/V). In another aspect, when deacylated gellan gum is prepared, deacylated gellan gum is added to ion exchange water or ultrapure water at 0.1% to 1% (W/V), preferably 0.2% to 0.8% (W/V), more preferably 0.3% to 0.6% (W/V).

Then, the aforementioned deacylated gellan gum is dissolved to a transparent state by stirring with heating at any temperature as long as dissolution is possible, which may be not less than 60° C., preferably not less than 80° C., more preferably not less than 90° C. (e.g., 80 to 130° C.). After dissolution, the mixture is allowed to cool with stirring, and sterilized with autoclave at, for example, 121° C. for 20 min.

After cooling to room temperature, for example, the aqueous solution is added to a liquid medium such as DMEM/F-12 medium with stirring by a homomixer and the like to a desired final concentration (e.g., when the final concentration is 0.015%, the ratio of 0.3% aqueous solution:medium is 1:19), and the mixture is homogeneously mixed. The mixing method of the aqueous solution and the medium is not particularly limited, and may be manual mixing such as pipetting etc., or mixing with an instrument such as magnetic stirrer, mechanical stirrer, homomixer and homogenizer. Furthermore, the medium composition in the present invention can be filtrated through a filter after mixing. The size of the pore of the filter to be used for the filtration treatment is 5 μm to 100 μm, preferably 5 μm to 70 μm, more preferably 10 μm to 70 μm.

Furthermore, after preparation of the medium composition of the present invention, the structure can be sedimented by a centrifugation treatment.

Preferable embodiments of the medium composition to be used in the present invention and a production method thereof are described below.

The medium composition to be used in the present invention is preferably a medium composition which enables culture of cells or tissues in suspension, which is characterized in that the medium composition has a viscosity of the aforementioned medium composition of not more than 8 mPa·s (under 37° C. conditions), and contains deacylated gellan gum or a salt thereof. In one embodiment, the concentration of deacylated gellan gum or a salt thereof in the medium composition is 0.005-0.3% (W/V) (preferably, 0.01-0.05% (W/V)). In one embodiment, the medium composition further contains a polysaccharide other than deacylated gellan gum or a salt thereof. In one embodiment, the medium composition contains divalent metal ions (e.g., calcium ion) at a concentration sufficient for deacylated gellan gum to form the structure which enables culture of cells or tissues in suspension. The concentration is, for example, 0.1 mM to 300 mM, preferably, 0.5 mM to 100 mM.

The medium composition can be produced by mixing deacylated gellan gum or a salt thereof and a medium. In one embodiment, the medium is a liquid medium. In one embodiment, the liquid medium contains divalent metal ions (e.g., calcium ion) at a concentration sufficient for deacylated gellan gum to form the structure which enables culture of cells or tissues in suspension. The concentration is, for example, 0.1 mM to 300 mM, preferably, 0.5 mM to 100 mM. In one embodiment, deacylated gellan gum or a salt thereof dissolved or dispersed in a solvent and a medium are mixed. In one embodiment, deacylated gellan gum or a salt thereof dissolved or dispersed in a solvent is sterilized. In one embodiment, sterilization is performed by autoclave sterilization. In another embodiment, sterilization is performed by filtration sterilization. In one embodiment, filtration sterilization is performed by passing through a 0.1-0.5 μm filter.

Those of ordinary skill in the art can freely select the form and state of the cells and/or tissues to be cultured in the present invention. Specific preferable examples thereof include, but are not particularly limited to, a state in which the cells and/or tissues are singly dispersed in the medium composition, a state in which the cells and/or tissues are attached to the surface of a carrier, a state in which the cells and/or tissues are embedded inside a carrier, a state in which plural cells assemble and form cell aggregates (spheres), or a state in which two or more kinds of cells assemble and form cell aggregates (spheres), and the like. More preferred are a state in which the cells and/or tissues are attached to the surface of a carrier, a state in which the cells and/or tissues are embedded inside a carrier, a state in which plural cells assemble and form cell aggregates (spheres), and a state in which two or more kinds of cells assemble and form cell aggregates (spheres). Further preferred are a state in which the cells and/or tissues are attached to the surface of a carrier, a state in which plural cells assemble and form cell aggregates (spheres), and a state in which two or more kinds of cells assemble and form cell aggregates (spheres). Among these states, the state with forming cell aggregates (spheres) can be mentioned as the most preferable state to be cultured by the culture method of the present invention, since cell-cell interactions and cell structures close to those in the in vivo environment are reconstructed, long-term culture can be performed while maintaining the cell function, and also cell recovery is relatively easy.

As a carrier to support the cells and/or tissues on the surface, microcarrier and glass bead composed of various polymers, ceramic bead and the like can be mentioned. As examples of the polymers, vinyl resin, urethane resin, epoxy resin, polystyrene, polymethylmethacrylate polyester, polyamide, polyimide, silicon resin, phenol resin, melamine resin, urea resin, aniline resin, ionomer resin, polycarbonate, collagen, dextran, gelatin, cellulose, alginates, mixtures thereof, and the like can be used. The carrier may be coated with a compound that enhances cell adhesion or release of substance from the cells. As examples of such coating materials, poly(monostearoylglyceride co-succinic acid), poly-D,L-lactid-co-glycolide, hyaluronate sodium, n-isopropylacrylamide, collagen I to XIX, fibronectin, vitronectin, laminin-1 to 12, nitrogen, tenascin, thrombospondin, von Willebrand factor, osteopontin, fibrinogen, various elastins, various proteoglycans, various cadherins, desmocolin, desmoglein, various integrins, E-selectin, P-selectin, L-selectin, immunoglobulin superfamily, Matrigel, poly-D-lysine, poly-L-lysine, chitin, chitosan, sepharose, alginic acid gel, various hydrogels, further, cleavage fragments thereof, and the like can be mentioned. Here, two or more kinds of the coating materials may be combined. Furthermore, one or more kinds of polysaccharides such as guargum, tamarind gum, locust bean gum, gum arabic, tara gum, tamarind gum, methylcellulose and the like can also be mixed with a medium to be used for culture of a carrier supporting the cells and/or tissues on the surface. The carrier may also contain a magnetic material, for example, ferrite. The diameter of the carrier is several tens of micrometers to several hundreds of micrometers, more preferably 100 μm to 200 μm, and its specific gravity is preferably close to 1, more preferably 0.9-1.2, particularly preferably about 1.0. Examples of the carrier include, but are not limited to, Cytodex 1 (registered trade mark), Cytodex 3 (registered trade mark), Cytoline 1 (registered trade mark), Cytoline 2 (registered trade mark), Cytopore 1 (registered trade mark), Cytopore 2 (registered trade mark), (above, GE Healthcare Life Sciences), Biosilon (registered trade mark) (NUNC), Cultispher-G (registered trade mark), Cultispher-S (registered trade mark) (above, Thermo SCIENTIFIC), HILLEXCT (registered trade mark), ProNectinF-COATED (registered trade mark), and HILLEXII (registered trade mark) (Solo Hill Engineering) and the like. The carrier may be sterilized as necessary. The sterilization method is not particularly limited and, for example, radiation sterilization, ethylene oxide gas sterilization, autoclave sterilization, dry heat sterilization, and the like can be mentioned. The method for culturing animal cells using the carrier is not particularly limited, and a culture method using a general flow layer-type culture vessel or filling layer-type culture vessel, and the like can be used. Here, a carrier supporting cells and/or tissues on the surface and using a medium composition comprising the structure of the particular compound of the present invention allows for uniform dispersion even without an operation of shaking and the like. As a result, the object cells and/or tissues can be cultured without losing cell function. The cells and/or tissues cultured by this method can be collected by performing centrifugation and filtration treatment while the cells and/or tissues are supported by the carrier after the culture. In this case, centrifugation and filtration treatment may be performed after adding the liquid medium used. For example, unlimitatively, the gravitational acceleration (G) of centrifugation is 100 G to 400 G, and the size of the pore of the filter used for the filtration treatment is 10 μm to 100 μm. Furthermore, cultured carriers can be recovered with a magnetic force by encapsulating a material having magnetism, such as ferrite, in the carrier. The cells and/or tissues cultured by this method can be collected by releasing the carrier by using various chelators, a heat treatment, or an enzyme.

When cells and/or tissues are embedded inside a carrier, materials composed of various polymers can be selected as the carrier. As examples of such polymers, collagen, gelatin, alginates, chitosan, agarose, poly glycolic acid, polylactic acid, fibrin adhesive, polylactic acid-polyglycolic acid copolymer, proteoglycan, glycosaminoglycan, sponge such as polyurethane foam, DseA-3D (registered trade mark), poly N-substituted acrylamide derivative, poly N-substituted methacrylamide derivative, and copolymers thereof, polyvinyl methylether, polypropylene oxide, polyethylene oxide, temperature sensitive polymers such as partially acetified poly(vinyl alcohol), polyacrylamide, poly(vinyl alcohol), methylcellulose, nitrocellulose, cellulose butyrate, polyethylene oxide, and hydrogels such as poly(2-hydroxyethylmethacrylate)/polycaprolactone and the like can be mentioned. In addition, it is possible to prepare a carrier for embedding cells by using two or more kinds of these polymers. Furthermore, the carrier may have a physiologically active substance besides these polymers. As examples of the physiologically active substance, cell growth factors, differentiation inducing factors, cell adhesion factors, antibodies, enzymes, cytokines, hormones, lectins, extracellular matrices and the like can be mentioned, and a plurality of these can also be contained. Furthermore, one or more kinds of thickeners such as guargum, tamarind gum, alginic acid propylene glycol ester, locust bean gum, gum arabic, tara gum, tamarind gum, methylcellulose and the like can also be mixed with a medium used for culture of a carrier embedding cells and/or tissues.

The method for embedding the cells and/or tissues in these carriers is not particularly limited and, for example, a method including aspirating a mixture of the cells and the aforementioned polymers with a syringe and dropwise adding them to a medium from around 25 G-19 G injection needle, or dropwise adding to a medium using a micropipette, and the like can be used. The size of the bead-like carrier formed here is determined by the shape of the tip of a tool used for the dropwise addition of a mixture of the cell and the aforementioned polymers, which is preferably several tens of micrometers to several thousands of micrometers, more preferably 100 μm to 2000 μm. The number of cells that can be cultured on a bead-like carrier is not particularly limited, and can be freely selected according to the bead size. For example, 5 million cells can be embedded in a bead-like carrier with a diameter of about 2000 μm. Within the carrier, the cells may be singly dispersed or plural cells may assemble to form a cell aggregate. Here, using a medium composition comprising the structure of the particular compound allows a carrier having the cells and/or tissues embedded therein to uniformly disperse even without an operation of stirring and the like. As a result, the object cells and/or tissues can be cultured without losing cell function. The cells and/or tissues cultured by this method can be collected by performing centrifugation and filtration treatment while the cells and/or tissues are embedded in the carrier after the culture. In this case, centrifugation and filtration treatment may be performed after adding the liquid medium used. For example, unlimitatively, the gravitational acceleration (G) of centrifugation is 100 G to 400 G, and the size of the pore of the filter used for the filtration treatment is 10 μm to 100 μm. The cells and/or tissues cultured by this method can be collected by dispersing them by decomposing the carrier by a treatment using various chelator s, heat, an enzyme and the like.

A method for forming a cell aggregate (sphere) is not particularly limited, and can be appropriately selected by those of ordinary skill in the art. Examples thereof include a method using a container having a cell non-adhesive surface, hanging drop method, gyratory culture method, three-dimensional scaffold method, centrifugation method, a method using coagulation by an electric field or magnetic field and the like. For example, using a method using a container having a cell non-adhesive surface, the object cells are cultured in a culture container applied with a surface treatment to inhibit cell adhesion, whereby a sphere can be formed. When such cell non-adhesive culture container is used, the object cells are first collected, a cell suspension thereof is prepared and plated in the culture container to perform culture. When culture is continued for about 1 week, the cells spontaneously form a sphere. As a cell non-adhesive surface used here, a surface of a culture container generally used such as schale and the like, which is coated with a substance inhibiting cell adhesion and the like can be used. Examples of such substance include agarose, agar, copolymer of poly-HEMA(poly-(2-hydroxylethylmethacrylate)2-methacryloyloxyethylphosphoryl choline and other monomer (e.g., butylmethacrylate etc.) and the like. When cytotoxicity is absent, the substance is not limited thereto.

As a method for forming a cell aggregate (sphere), the methods described in NATURE BIOTECHNOLOGY, VOL. 28, NO. 4, APRIL 2010, 361-366, NATURE PROTOCOLS, VOL. 6, NO. 5, 2011, 689-700, NATURE PROTOCOLS, VOL. 6, NO. 5, 2011, 572-579, Stem Cell Research, 7, 2011, 97-111, Stem Cell Rev and Rep, 6, 2010, 248-259 and the like can also be used.

In addition, a medium used for culture for forming a sphere can also contain a component that promotes formation of a sphere or promotes maintenance thereof. Examples of the component having such effect include dimethyl sulfoxide, superoxide dismutase, ceruloplasmin, catalase, peroxidase, L-ascorbic acid, L-ascorbic acid phosphate, tocopherol, flavonoid, uric acid, bilirubin, selenium-containing compound, transferrin, unsaturated fatty acid, albumin, theophylline, forskolin, glucagon, dibutyryl cAMP and the like. As the selenium-containing compound, ROCK inhibitors such as sodium selenite, sodium selenate, dimethyl selenide, hydrogen selenide, Selenomethionine, Se-Methylselenocysteine, Selenocystathionine, Selenocysteine, Selenohomocysteine, adenosine-5'-triphosphoric acid, Se-Adenosylselenomethionine, Y27632, Fasudil (HA1077), H-1152, Wf-536 and the like can be mentioned. To obtain the object cell aggregate having a uniform size, plural concaves having the same diameter as the object cell aggregate can also be introduced onto a cell non-adhesive culture container to be used. When these concaves are in contact with each other or within the range of the diameter of the object cell aggregate, and cells are plated, the plated cells do not form a cell aggregate between concaves but certainly form a cell aggregate with a size corresponding to the volume thereof in the concave, thus affording a cell aggregate population having a uniform size. As the shape of the concave in this case is preferably a hemisphere or cone.

Alternatively, a sphere can also be formed based on a support showing cell adhesiveness. Examples of such support include collagen, polyrotaxane, polylactic acid (PLA), polylactic acid glycolic acid (PLGA) copolymer, hydrogel and the like.

In addition, a sphere can also be formed by co-cultivating with a feeder cell. As a feeder cell to promote sphere formation, any adhesive cell can be used. Preferably, a feeder cell for each kind of cell is desirable. Although not limited, for example, when a sphere of cells derived from the liver or cartilage is formed, examples of the feeder cell include COS-1 cell and vascular endothelial cell as preferable cell types.

Furthermore, a sphere can also be formed using the culture composition containing the structure composed of the particular compound. In this case, the concentration of the particular compound is 0.0005% to 1.0% (W/V), preferably 0.001% to 0.3% (W/V), more preferably 0.005% to 0.1% (W/V), further preferably 0.01% to 0.05% (W/V). The sphere is prepared by uniformly dispersing the object cells in a medium containing the structure of the particular compound, and allowing them to culture by standing still for 3 days to 10 days. The prepared sphere can be recovered by centrifugation and filtration treatment. For example, unlimitatively, the gravitational acceleration (G) of centrifugation is 100 G to 400 G, and the size of the pore of the filter used for the filtration treatment is 10 μm to 100 μm. In addition, using magnetic fine particles coated, on the surface, with an antibody that specifically binds to the object cell, cultured sphere can be recovered by magnetic force. Examples of such magnetic fine particles include Dynabeads (manufactured by Veritas Ltd.), MACS microbead (manufactured by Miltenyi Biotec), BioMag (manufactured by Techno Chemicals Corporation) and the like.

The size of the sphere varies depending on the cell type and culture period and is not particularly limited. When it has a spherical shape or ellipse spherical shape, the diameter thereof is 20 μm to 1000 μm, preferably 40 μm to 500 μm, more preferably 50 μm to 300 μm.

Such sphere can maintain proliferative capacity for not less than 10 days, preferably not less than 13 days, more preferably not less than 30 days, by continuing the static culture. By regularly further performing, during the static culture, mechanical division, or a single cell-forming treatment and coagulation, the proliferative capacity can be maintained substantially infinitely.

The culture container to be used for culturing sphere is not particularly limited as long as it generally permits animal cell culture. For example, flask, dish, schale, tissue culture dish, multidish, microplate, microwell plate, multiplate, multiwell plate, chamber slide, schale, tube, tray, culture bag, roller bottle and the like can be mentioned.

The medium to be used for static culture of sphere can contain a cell adhesion factor, examples thereof include Matrigel, collagen gel, gelatin, poly-L-lysine, poly-D-lysine, laminin and fibronectin. Two or more kinds of these cell adhesion factors can also be added in combination.

Furthermore, the medium to be used for culturing sphere can be mixed with a thickener such as guargum, tamarind gum, alginic acid propylene glycol ester, locust bean gum, gum arabic, tara gum, tamarind gum, methylcellulose and the like.

Using a medium composition comprising the structure composed of the particular compound, uniform dispersion in a medium can be afforded even without an operation of shaking and the like. As a result, the object cells and/or tissues can be cultured as a sphere without losing cell function. The sphere statically cultured by this method can be collected by performing centrifugation or filtration treatment after the culture. In this case, centrifugation or filtration treatment may be performed after adding the liquid medium used. For example, unlimitatively, the gravitational acceleration (G) of centrifugation is 100 G to 400 G, and the size of the pore of the filter used for the filtration treatment is 10 μm to 100 μm. In addition, using magnetic fine particles coated, on the surface, with an antibody that specifically binds to the object cell, cultured sphere can be recovered by magnetic force. Examples of such magnetic fine particles include Dynabeads (manufactured by Veritas Ltd.), MACS microbead (manufactured by Miltenyi Biotec), BioMag (manufactured by Techno Chemicals Corporation) and the like. The recovered sphere can be dispersed as single cells by further decomposing by a treatment with various chelators, heat, filter, enzyme and the like.

As a method for static culture of plant-derived cells and/or tissues, callus, which is an undifferentiated plant cell aggregate, can be cultivated. Callus can be induced by a method known for each plant species to be used. For example, a surface of a part of a tissue of a differentiated plant body (e.g., root, stalk, leaf section, seed, growing point, embryo, pollen etc.) is sterilized, where necessary, with 70% alcohol, 1% sodium hypochlorite solution and the like, a tissue section with a suitable size (e.g., about 1-about 5 mm square root section) is cut out with a knife and the like, the tissue section is plated on a callus induction medium sterilized in advance by an aseptic operation using a clean bench and the like, and aseptically cultivated under suitable conditions. The callus induced here may be subjected to liquid culture for mass proliferation, or may also be maintained as a seed strain by passaging in a pass through medium. The pass through culture may be performed using any of liquid medium and solid medium.

The amount of the plant cell aggregate inoculated when starting the static culture using the medium composition varies depending on the proliferation rate of the object cell, culture manner (batch culture, fed-batch culture, continuous culture etc.), culture period and the like. For example, when a plant cell aggregate such as callus and the like is to be cultivated, it is inoculated to the medium composition such that the wet weight of the cell aggregate relative to the medium composition is 4-8 (W/V (w/v)) %, preferably 5-7 (w/v) %. The particle size of the plant cell aggregate during culture is 3 mm to 40 mm, preferably 3 mm to 20 mm, more preferably 5 mm to 15 mm. As used herein, the "particle size" means a diameter when, for example, the plant cell aggregate has a spherical shape, a major axis when it has an ellipse spherical shape, and the maximum length possible when it has other shape.

The temperature when cells and/or tissues are cultivated is generally 25 to 39° C., preferably 33 to 39° C., for animal cells. The $CO_2$ concentration is generally 4 to 10% by volume in the culture atmosphere, and 4 to 6 volume % is preferable. The culture period is generally 3 to 35 days, which may be freely set according to the object of the culture. The culture temperature for plant cells is generally 20 to 30° C. and, when light is necessary, they can be cultured under illuminance conditions of illuminance 2000-8000 lux. While the culture period is generally 3 to 70 days, which may be freely set according to the object of the culture.

When cells and/or tissues are cultured, cells and/or tissues prepared separately are added to the culture composition and mixed to give a uniform dispersion. In this case, the mixing method is not particularly limited and, for example, manual mixing using pipetting and the like, mixing using instrument such as stirrer, vortex mixer, microplate mixer, shaking machine and the like can be mentioned. After mixing, the culture medium may be stood still, or the culture medium may be rotated, shaken or stirred as necessary. The rotating speed and frequency can be appropriately set according to the object of those of ordinary skill in the art. When the medium composition needs to be exchanged during the static culture period, the cells and/or tissues and the medium composition are separated by centrifugation or filtration treatment, and a new medium composition can be added of the cells and/or tissues. Alternatively, the cells and/or tissues are appropriately concentrated by centrifugation or filtration treatment, and a new medium composition can be added to the concentrated liquid. For example, unlimitatively, the gravitational acceleration (G) of centrifugation is 100 G to 400 G, and the size of the pore of the filter used for the filtration treatment is 10 μm to 100 μm. In addition, using magnetic fine particles coated, on the surface, with an antibody that specifically binds to the object cell, the cultured cells and/or tissues can be separated by magnetic force. Examples of such magnetic fine particles include Dynabeads (manufactured by Veritas Ltd.), MACS microbead (manufactured by Miltenyi Biotec), BioMag (manufactured by Techno Chemicals Corporation) and the like. Exchange of the medium composition can also be performed by using a bioreactor and an automatic incubator capable of conducting under a mechanical control and under a closed environment.

Method for Isolating Cells or Tissues

The present invention provides a treatment method for efficiently isolating animal or plant cells and/or tissues from the aforementioned medium composition containing the animal or plant cells and/or tissues (i.e., culture preparation of cells or tissues in the aforementioned medium composition). The method of the present invention contains at least one step selected from the group consisting of the following (A), (B) and (C):

(A) passing a medium composition containing cells and/or tissues (i.e., culture preparation of cells or tissues) through a filter having fine pores having a size (pore diameter) of 5-500 μm, (B) adding a chelator to the culture preparation of the cells and/or tissues, and (C) diluting the culture preparation of the cells and/or tissues with a physiological aqueous solution.

Each step is explained below.

Step (A) Passage Through Filter

According to step (A), the "structure which enables cells or tissues to be cultured in suspension" contained in the medium composition is partially destroyed by passing the medium composition through a filter, and the recovery rate of the cells or tissues is considered to increase. Examples of animal or plant cells and tissues that can be used include all of those mentioned above (including spheres).

The size (pore diameter) of the fine pore of the filter is 5-500 μm, preferably 10-200 μm, more preferably 20-100 μm, further preferably 30-40 μm.

The pore diameter of the filter is preferably one that permits cells or tissues in the culture preparation to pass through. Here, the "size that permits cells or tissues to pass through" means a size that allows passage of cells or tissues while maintaining survival. For example, the "size that permits cells or tissues to pass through" encompasses not only when the pore diameter of the filter is larger than the diameter of the cells or tissues to be cultured but also an embodiment in which a cell aggregate, sphere or tissue in the culture preparation passes through a filter having a pore diameter smaller than the diameter thereof, whereby it is divided into multiple cells, cell aggregates, spheres or tissues while maintaining survival. While the size of the cell cannot be defined unconditionally since it depends on the kind of the cell, since a general cell having a diameter of about 7.5-20 μm can easily pass through a filter having a pore diameter of about 20-100 μm, preferably 30-40 μm, in a single cell state while maintaining good survival property, and further, the "structure which enables cells or tissues to be cultured in suspension" contained in the medium composition is efficiently destroyed, a good recovery rate is expected.

Examples of the material of the filter include, but are not particularly limited to, polyethylene, polypropylene, polyamide (nylon), polypropylene, acryl, polylactic acid, cellulose mixed ester, polycarbonate, polyester, glass and the like. While the properties such as polarity, chargeability, hydrophilicity and the like vary depending on the material, the correlation between these properties and the recovery rate is weak, and a good recovery rate is expected irrespective of the material used. Polyamide (nylon), polyethylene, polyester, glass and the like are preferable from the aspects of easy availability and the like.

As these filters, commercially available products may be used, and concrete examples thereof include CellTrics filter (trade mark) manufactured by Partec: pore diameter 5 μm (model number 06-04-004-2323), 10 μm (model number 06-04-004-2324), 20 μm (model number 06-04-004-2325), 30 μm (model number 06-04-004-2326), 50 μm (model number 06-04-004-2327), 100 μm (model number 06-04-004-2328) and 150 μm (model number 06-04-004-2329), Cell Strainer (trade mark) manufactured by Becton, Dickinson and Company: pore diameter 40 μm (model number 352340), 70 μm (model number 352350) and 100 μm (model number 352360), Filcon (trade mark) manufactured by AS ONE: pore diameter 20 μm (model number 2-7211-01), 30 μm (model number 2-7211-02), 50 μm (model number 2-7211-03), 70 μm (model number 2-7211-04), 100 μm (model number 2-7211-05) and 200 μm (model number 2-7211-06) and the like.

While the number of passages through the filter may be one, it is possible to improve the recovery rate of cells or tissues by passing them through the filter multiple times. The number of passages through the filter is generally 1-10, preferably 3-8, more preferably 3-5.

For passing through a filter multiple times, an operation including passing a culture preparation of cells or tissues through a single filter and collecting the passed suspension may be carried out a plurality of times, or a culture preparation of cells or tissues may be passed through a multiple filter containing a plurality of filter membranes (e.g., 3-5 filter membranes) layered together. The use of a multiple layered filter is advantageous from the viewpoint of operation efficiency. For passage through a filter multiple times, a plurality of filters having the same pore diameter may be used, or a plurality of filters having different pore diameters may be used in combination. Preferably, a plurality of filters (e.g., 3-5 filters) having the same pore diameter (e.g., 30-40 μm) are used.

Step (B) Chelator Addition

According to step (B), it is expected that, by the addition of a chelator to the aforementioned medium composition, the metal cations (preferably divalent metal ions such as calcium ion, magnesium ion and the like) are removed from the "structure which enables cells or tissues to be cultured in suspension" contained in the medium composition, the association between particular compounds (e.g., deacylated gellan gum) via a metal cation in the structure becomes loose and the "structure which enables cells or tissues to be cultured in suspension" is partially destroyed, whereby the recovery rate of the cells or tissues is improved.

While the chelator is not particularly limited as long as it is a compound capable of forming a complex with a divalent metal ion such as calcium ion, magnesium ion and the like (preferably, calcium ion). Examples thereof include citric acid or a salt thereof (e.g., trisodium citrate); EDTA or a salt thereof (e.g., sodium edetates such as EDTA2Na, EDTA3Na, EDTA4Na and the like); salts of hydroxyethylethylenediamine triacetic acid such as HEDTA3Na and the like; EGTA or a salt thereof; pentetate (salts of diethylenetriamine pentaacetic acid); phytic acid; phosphonic acid such as etidronic acid and the like and salts thereof including sodium salt; sodium oxalate; polyamino acids such as polyaspartic acid, polyglutamic acid and the like; sodium polyphosphate; sodium metaphosphate; phosphoric acid; alanine; dihydroxyethylglycine; gluconic acid; ascorbic acid; succinic acid; tartaric acid and the like. To improve recovery rates of cells or tissues, citric acid or a salt thereof (e.g., trisodium citrate) or EDTA or a salt thereof (e.g., sodium edetates such as EDTA2Na, EDTA3Na, EDTA4Na and the like) is preferable, and citric acid or a salt thereof (e.g., trisodium citrate) is most preferable.

The amount of a chelator to be added is an amount capable of loosening the association between particular compounds (e.g., deacylated gellan gum) via a metal cation in the "structure which enables cells or tissues to be cultured in suspension" contained in the aforementioned medium composition. For example, in the case of citric acid or a salt thereof (e.g., trisodium citrate), it is generally not less than 2.4 mM, preferably, not less than 10 mM, as the final concentration immediately after addition. Theoretically, the upper limit is a saturated concentration of citric acid or a salt thereof. When the concentration is too high, an influence on the survival of cells or tissues is feared. Therefore, it is generally not more than 30 mM, more preferably not more than 15 mM. Thus, a preferable amount citric acid or a salt thereof to be added is 2.4-30 mM, more preferably 10-15 mM, as the final concentration immediately after addition. A preferable concentration can be achieved by adding 3.12-3.8 (W/V) % aqueous trisodium citrate solution, which is commercially available as an anticoagulant, at ¹⁄₁₀ volume relative to the culture preparation as 1.

After addition of the chelator to the aforementioned culture preparation, the obtained mixture is preferably stirred well by inversion mixing, vortexing and the like to disperse the chelator uniformly. The stirring time is generally 30 sec-1 min.

The recovery rate of the cells or tissues can be increased by continuously stirring the mixture containing the chelator dispersed uniformly. Examples of the stirring method include inversion mixing, stirring bar, vortex and the like and are not particularly limited. To avoid an adverse influence on the viability of cells or tissues, a relatively mild method such as inversion mixing, stirring bar and the like is preferable. The stirring time is not particularly limited as long as the cell recovery rate can be increased, and is generally not less than 10 min. The longer the stirring time is, the higher the recovery rate is. Therefore, to increase the recovery rate, a longer stirring time is better. On the other hand, to avoid an adverse influence on the survival of the cells or tissues, the stirring time is preferably not more than 60 min, more preferably not more than 30 min. Such long-term stirring is effective for improving the recovery rate particularly when filtration is not used in combination.

When a mixture containing a chelator dispersed uniformly is statically stood without stirring, the recovery rate of the cells or tissues may decrease conversely. Thus, it is preferable to avoid statically standing.

Step (C) Dilution

According to step (C), it is expected that, dilution of the aforementioned medium composition with a physiological aqueous solution decreases the concentration of the "structure which enables culture of the cells or tissues in suspension" contained in the medium composition to decrease the ability to suspend the cells or tissues, as a result of which the recovery rate of the cells or tissues is improved.

The physiological aqueous solution to be used for the dilution is preferably isotonic with the cells or tissues in the culture preparation. As such physiological aqueous solution, liquid medium, balanced salt solution, saline and the like can be mentioned. As the liquid medium, a medium that can be used for preparing the medium composition which enables culture of the above-mentioned cells or tissues in suspension can be mentioned. In one embodiment, in the dilution step, the same liquid medium as the medium used for the medium composition containing the cells or tissues is added. Examples of the balanced salt solution include (Dulbecco) PBS ((Dulbecco's) Phosphate Buffered Saline), TBS (Tris Buffered Saline), EBSS (Earle's Balanced Salt Solution), GBSS (Gey's Balanced Salt Solution), HESS (Hank's Buffered Salt Solution), RBSS (Ringer's Balanced Salt Solution), SBSS (Simm's Balanced Salt Solution), TBSS (Tyrode's Balanced Salt Solution), Alsever's Solution, Puck's Balanced Salt Solution and the like.

The physiological aqueous solution to be used for dilution is preferably substantially free of calcium ion and magnesium ion. Using a physiological aqueous solution substantially free of calcium ion and magnesium ion, calcium ion concentration and magnesium ion concentration of the medium composition decrease, metal cations (preferably, divalent metal ions such as calcium ion, magnesium ion and the like) are removed from the "structure which enables cells or tissues to be cultured in suspension", the association between particular compounds (e.g., deacylated gellan gum) via a metal cation in the structure becomes loose, the "structure which enables cells or tissues to be cultured in suspension" is partially destroyed, and the recovery rate of the cells or tissues is considered to improve. Being "substantially free of calcium ion and magnesium ion" means that the calcium ion concentration and the magnesium ion concentration are each not more than 0.001 mM. The concentration of the calcium ion and magnesium ion in a physiological aqueous solution to be used for dilution is preferably not more than 0.0001 mM, more preferably not more than 0.00001 mM, most preferably 0 mM.

The physiological aqueous solution to be used for dilution is preferably substantially free of divalent metal ions including calcium ion and magnesium ion. Examples of the divalent metal ions include calcium ion and magnesium ion, as well as zinc ion, barium ion, manganese ion, cobalt ion, nickel ion, copper ion, iron ion and the like. Being "substantially free of divalent metal ions" means that the total concentration of the divalent metal ions is not more than 0.001 mM. The total concentration of the divalent metal ions in the physiological aqueous solution to be used for dilution is preferably not more than 0.0001 mM, more preferably not more than 0.00001 mM, most preferably 0 mM.

The physiological aqueous solution to be used for dilution may contain serum (FBS etc.), albumin and the like to increase the survival rate of cells or tissues.

The dilution rate in the dilution step is preferably 2 or more, when the dilution rate of a case where a physiological aqueous solution having the same volume as the volume of the medium composition containing cells or tissues (i.e., culture preparation of the cells or tissues) is added is defined as 2. The higher the dilution rate, the more the recovery rate is improved. To improve the recovery rate, higher dilution rate is preferable. However, when the dilution rate is too high, handling may be hindered since the entire volume becomes too large. Therefore, the dilution rate is generally, 2-10, preferably 2-5.

Preferable embodiments of each of steps (A), (B) and (C) are as described below.

(AA) A culture preparation of cells or tissues is passed through a filter having fine pores having a pore diameter of 5-500 µm (preferably 10-200 µm, more preferably 20-100 µm, further preferably 30-40 µm) plural times (preferably 3-8 times, more preferably 3-5 times). Preferably, the filtration is performed by passing the culture preparation of cells or tissues through a plurality of filter membranes (preferably 3-8, more preferably 3-5 filters) layered together.

(BB) Citric acid or a salt thereof (e.g., trisodium citrate) is added to the culture preparation of the cells or tissues. Preferably, the obtained mixture is stirred for not less than 10 min (e.g., 10-60 min, preferably 10-30 min).

(CC) The culture preparation of the cells or tissues is diluted with a physiologically balanced salt solution (e.g., (Dulbecco)PBS) substantially free of calcium ion and magnesium ion (preferably, substantially free of divalent metal ions) at a dilution rate of 2-10 (preferably 2-5).

In one embodiment, a medium composition containing the cells or tissues to be subjected to the method of the present invention (i.e., a culture preparation of cells or tissues) contains a protein (e.g., serum albumin) at a concentration of not less than 0.1 (w/v) %. When the method of the present invention contains step (B) and/or step (C), a medium composition containing the cells or tissues to be subjected to the method of the present invention (i.e., a culture preparation of cells or tissues) contains protein (e.g., serum albumin) at a concentration of preferably not less than 0.1 (w/v) %. When a protein is contained at said concentration, the recovery rate of the cells or tissues can be expected to increase as compared to the absence of the protein. The protein concentration of the medium composition containing the cells or tissues is not less than 0.1 (w/v) %, preferably not less than 0.2 (w/v) %. The higher the protein concentration, the higher the recovery rate of cells or tissues can be expected. While the upper limit of the protein concentration is theoretically the solubility of the protein, not more than 5 (w/v) %, preferably not more than about 2 (w/v) %, is preferable from the aspects of cost and the like. Since the protein concentration of the serum (e.g., FBS) is generally about 5 (w/v) %, a serum concentration of 2 (v/v) % corresponds to a protein concentration of 0.1 (w/v) %. Therefore, when the serum concentration of the medium composition containing the cells or tissues is not less than 2 (v/v) %, preferably not less than 4 (v/v) % (e.g., not less than 10 (v/v) %), it can be estimated that a protein is contained at a concentration that increases the recovery rate of the cells or tissues. Therefore, for example, when cells or tissues are cultured in the aforementioned medium composition (e.g., serum-free medium composition) having a protein concentration of less than 0.1 (w/v) %, and the obtained culture is subjected to the method of the present invention, a protein (e.g., serum albumin, serum etc.) may be added to the culture such that the protein concentration of the medium composition is not less than 0.1 (w/v) %, preferably not less than 0.2 (w/v) %.

Combination of Steps (A)-(C)

By combining 2 or 3 (i.e., all) steps selected from the group consisting of the above-mentioned (A), (B) and (C), the recovery rate of the cells or tissues is expected to be improved than when any one step is performed alone. As a combination of 2 steps, combination of (A) and (B), combination of (B) and (C), combination of (A) and (C) (e.g., combination of (AA) and (BB), combination of (BB) and (CC), combination of (AA) and (CC)) can be mentioned.

The order of steps when 2 or 3 steps are combined is not particularly limited. When steps (A) and (B) are combined, any of the orders of (A)→(B) and (B)→(A) (e.g., (AA)→(BB) and (BB)→(AA)) may be adopted. When steps (B) and (C) are combined, any of the orders of (B)→(C) and (C)→(B) (e.g., (BB)→(CC) and (CC)→(BB)) may be adopted. When steps (A) and (C) are combined, any of the orders of (A)→(C) and (C)→(A) (e.g., (AA)→(CC) and (CC)→(AA)) may be adopted. When all steps (A), (B) and (C) are combined, any of the orders of (A)→(B)→(C), (A)→(C)→(B), (B)→(A)→(C), (B)→(C)→(A), (C)→(A)→(B) and (C)→(B)→(A) (e.g., (AA)→(BB)→(CC), (AA)→(CC)→(BB), (BB)→(AA)→(CC), (BB)→(CC)→(AA), (CC)→(AA)→(BB) and (CC)→(BB)→(AA)) may be adopted.

In an embodiment including step (A) and step (B), a high recovery rate can be achieved even without stirring for not less than 10 min in step (B).

To improve the recovery rate, all steps (A), (B) and (C) are preferably performed in combination.

When all steps (A), (B) and (C) are performed in combination, the order of (A)→(B)→(C) (e.g., (AA)→(BB)→(CC)) is preferable for improving the recovery rate.

After the aforementioned pre-treatment step, the resultant mixture containing cells or tissues is subjected to centrifugation or a filtration treatment to remove fractions other than cells or tissues, and finally, cells and/or tissues can be isolated from the culture preparation of the cells or tissues. Techniques for precipitating cells or tissues by centrifugation are well known to those of ordinary skill in the art and appropriate conditions can be set by those of ordinary skill in the art according to the type of cell or tissue. In general, cells or tissues can be precipitated and separated from the supernatant by centrifugation with a centrifugal force of about 300-500 G.

Reagent for Isolating Cells or Tissues

In addition, the present invention provides a reagent for isolating cells or tissues from a culture preparation of the cells or tissues in a medium composition which enables culture of the cells or tissues in suspension, which comprises at least one element selected from the group consisting of the following (A'), (B') and (C'):
(A') a filter having fine pores having a pore diameter of 5-500 μm,
(B') a chelator, and
(C') a physiological aqueous solution.

By using the reagent of the present invention, cells or tissues can be isolated from a culture preparation of the cells or tissues in a medium composition which enables culture of the cells or tissues in suspension by performing the above-mentioned method of the present invention. The element (A') corresponds to an embodiment including step (A), the element (B') corresponds to an embodiment including step (B), and element (C') corresponds to an embodiment including step (C). The definition of each term is as described in the aforementioned "Method for isolating cells or tissues".

Preferable embodiments of each of elements (A'), (B') and (C') are as described below.

(AA') A filter having fine pores having a pore diameter of 5-500 μm (preferably 10-200 μm, more preferably 20-100 μm). To enable plural times (preferably 3-8 times, more preferably 3-5 times) of filtration, it may be a combination of a plurality of filters (single membranes) (preferably 3-8, more preferably 3-5 filters), or a multiple filter containing a plurality of filter membranes (preferably 3-8, more preferably 3-5 filter membranes) layered together.

(BB') citric acid or a salt thereof (e.g., trisodium citrate).

(CC') diluted with a physiologically balanced salt solution (e.g., (Dulbecco)PBS) substantially free of calcium ion and magnesium ion (preferably, substantially free of divalent metal ions) at a dilution rate of 2-10 (preferably 2-5).

The reagent of the present invention may contain 2 or 3 (i.e., all) elements selected from the group consisting of the above-mentioned (A'), (B') and (C') in combination. Each element may be placed in each independent container, and all elements are placed in one package to give a kit. As a combination of 2 elements, combination of (A') and (B'), combination of (B') and (C'), combination of (A') and (C') (e.g., combination of (AA') and (BB'), combination of (BB') and (CC'), combination of (AA') and (CC')) can be mentioned. Using the reagent of the present invention containing 2 or 3 of the aforementioned elements in combination, the method of the present invention including a combination of the corresponding 2 or 3 steps can be performed.

In a preferable embodiment, the reagent of the present invention contains elements (A'), (B') and (C') (e.g., (AA'), (BB') and (CC')).

The reagent of the present invention may further contain the above-mentioned particular compound (e.g., deacylated gellan gum or a salt thereof) for preparing a medium composition which enables culture of the cells or tissues in suspension. Using the reagent of the present invention in such embodiment, the user can prepare a medium composition which enables culture of the cells or tissues in suspension by using the particular compound (e.g., deacylated gellan gum or a salt thereof), culture the desired cells or tissues in suspension in the medium composition, and isolate the cells or tissues from the obtained culture preparation of the cells or tissues by the above-mentioned method of the present invention.

The particular compound (e.g., deacylated gellan gum or a salt thereof) may be contained as an isolated compound or an aqueous solution in the reagent of the present invention, or may be contained in an embodiment of a medium composition which enables culture of the cells or tissues in suspension, in the reagent of the present invention. The medium composition optionally contains a protein (e.g., serum albumin, serum) at a concentration of not less than 0.1 (w/v) %, preferably not less than 0.2 (w/v) %. Alternatively, the reagent of the present invention may contain a protein (e.g., serum albumin, serum) to adjust the protein concentration of the culture after cultivation to not less than 0.1 (w/v) %, preferably not less than 0.2 (w/v) %.

The present invention is explained in more detail in the following by specifically describing an Example of the medium composition of the present invention, which is not to be construed as limitative.

EXAMPLES

[Example 1] Cell Recovery Test by Dilution Using Filters in Combination

A medium composition of DMEM (manufactured by Wako Pure Chemical Industries, Ltd.) containing 0.015% (w/v) deacylated gellan gum (KELCOGEL CG-LA, manufactured by Sansho Co., Ltd.) and 10% (v/v) fetal bovine serum was prepared by a homomixer according to the method of patent document 1. Human megakaryoblastic leukemia MEG01 cells (manufactured by DS Pharma Biochemical) was added to a cell concentration of 100,000 cells/mL, and the mixture was passed through a nylon filter Cell Strainer (trade mark) (pore diameter 40 μm, manufactured by Becton, Dickinson and Company) 3 times to give a cell suspension.

The above-mentioned cell suspension was dispensed to three 50 mL tubes by 5 mL each. Furthermore, deacylated gellan gum-free DMEM was added by 20 mL to dilute the first cell suspension, 5 mL to dilute the second cell suspension, and 0 mL (no addition) to the third cell suspension, and the mixtures were mixed by inversion 20 times. Each tube was subjected to a centrifugation treatment at 500 G for 10 min to precipitate the cells, and the supernatant was removed. The cells of each tube were resuspended in DMEM (1 mL), 10 μL was separated, mixed with an equal amount of Trypan Blue Stain 0.4% (manufactured by Invitrogen), the recovered viable cells were counted by a full automatic cell counter (TC20, manufactured by Bio-Rad) to measure the recovery rate.

For a case using a filter having a pore diameter of 100 μm, the same procedure as the above was performed to measure the recovery rate.

Moreover, for a case without passing through a filter, the same procedure as the above was performed to measure the recovery rate.

As a positive control, human megakaryoblastic leukemia MEG01 cells (manufactured by DS Pharma Biochemical) were suspended in deacylated gellan gum-free DMEM at the above-mentioned concentration. Then, cells were precipitated by a centrifugation treatment at 500 G for 10 min, and the supernatant was removed. The cells were resuspended in DMEM (1 mL), 10 μL was separated, mixed with an equal amount of Trypan Blue Stain 0.4% (manufactured by Invitrogen), the recovered viable cells were counted by a full automatic cell counter (TC20, manufactured by Bio-Rad) to measure the recovery rate.

The cell recovery rate under respective conditions is shown in Table 1 where the recovery rate of the positive control is taken as 100. When diluted 2-fold or 5-fold, cell recovery rate was increased after passing the suspension through the filter, and it was suggested that the method of the present invention is useful for improving a rate of cell recovery from a deacylated gellan gum-containing medium.

TABLE 1

| | positive control | deacylated gellan gum addition group | | |
| --- | --- | --- | --- | --- |
| filter pore diameter | | 40 μm | | 100 μm |

TABLE 1-continued

| | positive control | deacylated gellan gum addition group | | | | | | | |
| --- | --- | --- | --- | --- | --- | --- | --- | --- | --- |
| dilution rate | 1 | 5 | 2 | 1 | 5 | 2 | 1 | 5 | 2 | 1 |
| cell recovery rate (%) | 100 | 73 | 45 | 16 | 56 | 46 | 15 | 37 | 18 | 13 |

[Example 2] Effect of Filtration on Cell Recovery

A medium composition of IMDM (Iscove's Modified Dulbecco's Medium) (manufactured by Sigma-Aldrich) containing 0.015% (w/v) deacylated gellan gum (KELCOGEL CG-LA, manufactured by Sansho Co., Ltd) and 10% (v/v) fetal bovine serum and 10 ng/mL TPO (Thrombopoietin, manufactured by Peprotech) was prepared according to the method of patent document 1. To the above-mentioned medium was added TPO-dependent human megakaryoblastic leukemia cell line (UT-7/TPO; non-patent document: Komatsu et al., Blood. 1996, 87:4552-4560.) to a cell concentration of 20,000 cells/mL, dispensed to a 6-well plate and cultured for 3 days in a 37° C. $CO_2$ incubator at 5% $CO_2$ concentration.

After culture, the above-mentioned cell suspension was dispensed to three 15 mL tubes by 9.5 mL each. The first cell suspension was passed through a commercially available filter, CellTrics (trade mark) (manufactured by PARTEC, pore diameter 30 μm, nylon), 3 times. The second cell suspension was passed through a commercially available filter, Filcon S (trade mark) (manufactured by AS ONE, pore diameter 20 μm, polyethylene), 3 times. The third cell suspension was passed through a commercially available filter, Cell Strainer (trade mark) (manufactured by Becton, Dickinson and Company, pore diameter 40 μm, nylon), which is 3 times.

Each tube was subjected to a centrifugation treatment at 500 G for 10 min to precipitate the cells, and the supernatant was removed. The cells of each tube were resuspended in IMDM (0.5 mL), 10 μL was separated, mixed with an equal amount of Trypan Blue Stain 0.4% (manufactured by Invitrogen), the recovered viable cells were counted by a full automatic cell counter (TC20, manufactured by Bio-Rad) to measure the recovery rate.

For a case where the cell suspension was passed through a filter having a pore diameter of 30 μm once, the same procedure as the above was performed, and the recovery rate was measured.

Moreover, even for a case without passing through a filter, the same procedure as the above was performed, and the recovery rate was measured.

As a result, the cell recovery rate was increased after passing the suspension through the filter, and it was suggested that the method of the present invention is useful for improving a rate of cell recovery from a deacylated gellan gum-containing medium. The recovery rate is shown in Table 2 where the number of cells contained in the suspension was taken as 100.

TABLE 2

| deacylated gellan gum content | 0.015% | | |
| --- | --- | --- | --- |
| filter pore diameter | 30 μm | 20 μm | 40 μm |
| number of passage | 1 3 | 3 | 3 |

TABLE 2-continued

| cell recovery rate (%) | 2 | 1 | 47 | 91 | 95 |

[Example 3] Effect of Filtration on Cell Recovery

Using 0.020% (w/v) deacylated gellan gum (KELCOGEL CG-LA, manufactured by Sansho Co., Ltd.), the recovery rate was measured according to a method similar to that in Example 2.

For cases where the cell suspension was passed through a filter having a pore diameter of 30 µm once and 5 times, the same procedure as the above was performed, and the recovery rate was measured.

Moreover, even for a case without passing through a filter, the same procedure as the above was performed, and the recovery rate was measured.

As a result, the cell recovery rate was increased after passing the suspension through the filter, and it was suggested that the method of the present invention is useful for improving a rate of cell recovery from a deacylated gellan gum-containing medium. The recovery rate is shown in Table 3 where the number of cells contained in the suspension was taken as 100.

TABLE 3

| deacylated gellan gum content | 0.020% | | | | | |
|---|---|---|---|---|---|---|
| filter pore diameter | | 30 µm | | 20 µm | 40 µm |
| number of passage | | 1 | 3 | 5 | 3 | 3 |
| cell recovery rate (%) | 3 | 6 | 13 | 70 | 75 | 87 |

[Example 4] Effect of Composition of Diluting Solution on Cell Recovery Rate

A medium composition of DMEM (manufactured by Wako Pure Chemical Industries, Ltd.) containing 0.015% (w/v) deacylated gellan gum (KELCOGEL CG-LA, manufactured by Sansho Co., Ltd.) and 10% (v/v) fetal bovine serum) was prepared by a homomixer according to the method described in patent document 1. Thereto were added human megakaryoblastic leukemia MEG01 cells (manufactured by DS Pharma Biochemical) to a cell concentration of 100,000 cells/mL.

The above-mentioned cell suspension was dispensed to a 50 mL tube by 5 mL. Furthermore, deacylated gellan gum-free DMEM (manufactured by Wako Pure Chemical Industries, Ltd.), RPMI-1640 (manufactured by Wako Pure Chemical Industries, Ltd.), or D-PBS(-) (manufactured by Wako Pure Chemical Industries, Ltd.) was added by 20 mL or 0 mL (no addition) per one tube of cell suspension to dilute the suspension, and the mixture was mixed by inversion at 20 times. DMEM contains $CaCl_2$ (anhyd.) (200 mg/ml) and $MgSO_4$ (anhyd.) (97.67 mg/ml) as calcium salt and magnesium salt. On the other hand, RPMI-1640 contains $CaCl_2$ (anhyd.) (100 mg/ml) and $MgSO_4$ (anhyd.) (48.84 mg/ml) as calcium salt and magnesium salt. D-PBS (-) does not contain calcium salt and magnesium salt. Therefore, the divalent metal ion (calcium ion and magnesium ion) concentration is lower in the order of D-PBS(-) <RPMI-1640 medium<DMEM. Each tube was subjected to a centrifugation treatment at 500 G for 10 min to precipitate the cells, and the supernatant was removed. The cells of each tube were resuspended in DMEM (1 mL), 10 µL was separated, mixed with an equal amount of Trypan Blue Stain 0.4% (manufactured by Invitrogen), the recovered viable cells were counted by a full automatic cell counter (TC20, manufactured by Bio-Rad) to measure the recovery rate.

As a positive control, human megakaryoblastic leukemia MEG01 cells (manufactured by DS Pharma Biochemical) were suspended in deacylated gellan gum-free DMEM at the above-mentioned concentration. Then, cells were precipitated by a centrifugation treatment at 500 G for 10 min, and the supernatant was removed. The cells were resuspended in DMEM (1 mL), 10 µL was separated, mixed with an equal amount of Trypan Blue Stain 0.4% (manufactured by Invitrogen), the recovered viable cells were counted by a full automatic cell counter (TC20, manufactured by Bio-Rad) to measure the recovery rate.

The cell recovery rate under respective conditions is shown in Table 4 where the recovery rate of the positive control is taken as 100. The cell recovery rate becomes higher in descending order of Ca and Mg concentrations in the diluting solution, the cell recovery rate was the highest in D-PBS(-), and it was suggested that the method of the present invention is useful.

TABLE 4

| | positive control | deacylated gellan gum addition group | | | |
|---|---|---|---|---|---|
| diluting solution | DMEM | none | D-PBS (—) | RPMI | DMEM |
| dilution rate | 1 | 1 | 5 | 5 | 5 |
| cell recovery rate (% control) | 100 | 13 | 64 | 53 | 44 |

[Example 5] Cell Recovery Test Using Chelator

A medium composition of DMEM (manufactured by Wako Pure Chemical Industries, Ltd.) containing 0.015% (w/v) deacylated gellan gum (KELCOGEL CG-LA, manufactured by Sansho Co., Ltd.) and 10% (v/v) fetal bovine serum) was prepared by a homomixer according to the method described in patent document 1. Thereto were added human megakaryoblastic leukemia MEG01 cells (manufactured by DS Pharma Biochemical) to a cell concentration of 100,000 cells/mL.

The above-mentioned cell suspension was dispensed to a 50 mL tube by 5 mL. A 3.8% (w/v) (129.2 mM) aqueous trisodium citrate dihydrate solution (0.5 mL) was added to the citric acid addition group (final concentration 0.35% (w/v) (12 mM)), and the mixture was stirred by vortex for 20 sec (N-20 M, manufactured by Nissin Rika). Furthermore, D-PBS(-) (manufactured by Wako Pure Chemical Industries, Ltd.) was added by 20 mL or 0 mL (no addition) per one tube of cell suspension to dilute the suspension, and the mixture was mixed by inversion at 20 times. Thereafter, for the filtration group, the suspension was passed through a nylon filter Cell Strainer (trade mark) (pore diameter 40 µm, manufactured by Becton, Dickinson and Company) 3 times to give a cell suspension. Each tube was subjected to a centrifugation treatment at 500 G for 10 min to precipitate the cells, and the supernatant was removed. The cells of each tube were resuspended in DMEM (1 mL), 10 µL was separated, mixed with an equal amount of Trypan Blue Stain 0.4% (manufactured by Invitrogen), the recovered viable cells were counted by a full automatic cell counter (TC20, manufactured by Bio-Rad) to measure the recovery rate.

As a positive control, human megakaryoblastic leukemia MEG01 cells (manufactured by DS Pharma Biochemical) were suspended in deacylated gellan gum-free DMEM at the above-mentioned concentration. Then, cells were precipitated by a centrifugation treatment at 500 G for 10 min, and the supernatant was removed. The cells were resuspended in DMEM (1 mL), 10 μL was separated, mixed with an equal amount of Trypan Blue Stain 0.4% (manufactured by Invitrogen), the recovered viable cells were counted by a full automatic cell counter (TC20, manufactured by Bio-Rad) to measure the recovery rate.

The cell recovery rate under respective conditions is shown in Table 5 where the recovery rate of the positive control is taken as 100. With the addition of trisodium citrate, the cell recovery rate reached not less than 80%. When compared to a case where D-PBS(−) dilution alone was performed, not less than twice as many cells were obtained, and it was suggested that the cell recovery method using a chelator is useful.

TABLE 5

| | positive control | deacylated gellan gum addition group | | | | |
|---|---|---|---|---|---|---|
| number of filtration | 0 | 0 | 0 | 3 | 0 | 3 |
| additive | none | none | none | none | citric acid | citric acid |
| dilution rate | 1 | 1 | 5 | 5 | 5 | 5 |
| cell recovery rate (% control) | 100 | 2 | 34 | 77 | 84 | 85 | after, the cell suspension was stirred in a shaker (manufactured by TAITEC, Bio Shaker, BR-30) at 120 rpm for 0, 10 or 30 min. Furthermore, D-PBS(−) (manufactured by Wako Pure Chemical Industries, Ltd.) was added by 20 mL or 0 mL (no addition) per one tube of cell suspension to dilute the suspension, and the mixture was mixed by inversion 20 times. Each tube was subjected to a centrifugation treatment at 500 G for 10 min to precipitate the cells, and the supernatant was removed. The cells of each tube were resuspended in DMEM (1 mL), 10 μL was separated, mixed with an equal amount of Trypan Blue Stain 0.4% (manufactured by Invitrogen), the recovered viable cells were counted by a full automatic cell counter (TC20, manufactured by Bio-Rad) to measure the recovery rate.

As a positive control, human megakaryoblastic leukemia MEG01 cells (manufactured by DS Pharma Biochemical) were suspended in deacylated gellan gum-free DMEM at the above-mentioned concentration. Then, cells were precipitated by a centrifugation treatment at 500 G for 10 min, and the supernatant was removed. The cells were resuspended in DMEM (1 mL), 10 μL was separated, mixed with an equal amount of Trypan Blue Stain 0.4% (manufactured by Invitrogen), the recovered viable cells were counted by a full automatic cell counter (TC20, manufactured by Bio-Rad) to measure the recovery rate.

The cell recovery rate under respective conditions is shown in Table 6 where the recovery rate of the positive control is taken as 100. While the cell recovery rate was increased by using any chelator, the cell recovery rate-increasing effect was stronger with trisodium citrate than EDTA. In addition, the cell recovery rate was further increased by continuous stirring after addition of the chelator.

TABLE 6

| | positive control | deacylated gellan gum addition group | | | | | | | | | |
|---|---|---|---|---|---|---|---|---|---|---|---|
| chelator | none | | | none | | | citric acid | | | EDTA | |
| dilution rate | 1 | 1 | 5 | 5 | 5 | 5 | 5 | 5 | 5 | 5 | 5 |
| stirring time (min) | 0 | 0 | 0 | 10 | 30 | 0 | 10 | 30 | 0 | 10 | 30 |
| cell recovery rate (% control) | 100.0 | 5.4 | 27.7 | 27.0 | 29.6 | 33.2 | 41.8 | 53.5 | 28.4 | 31.0 | 33.6 |

[Example 6] Study of Kind of Chelator and Stirring Time

A medium composition of DMEM (manufactured by Wako Pure Chemical Industries, Ltd.) containing 0.015% (w/v) deacylated gellan gum (KELCOGEL CG-LA, manufactured by Sansho Co., Ltd.) and 10% (v/v) fetal bovine serum) was prepared by a homomixer according to the method described in patent document 1. Thereto were added human megakaryoblastic leukemia MEG01 cells (manufactured by DS Pharma Biochemical) to a cell concentration of 100,000 cells/mL.

The above-mentioned cell suspension was dispensed to a 50 mL tube by 5 mL. As a chelator, 0.5 mL of an aqueous trisodium citrate dihydrate solution (3.8% (w/v) (129.2 mM)) or EDTA aqueous solution (11 mM) was added, and the mixture was mixed by inversion 20 times. The final concentration of each chelator at this time point was 0.35% (w/v) (12 mM) (trisodium citrate) or 1 mM (EDTA). There-

[Example 7] Study of Chelator Addition Conditions

A medium composition of DMEM (manufactured by Wako Pure Chemical Industries, Ltd.) containing 0.015% (w/v) deacylated gellan gum (KELCOGEL CG-LA, manufactured by Sansho Co., Ltd.) and 10% (v/v) fetal bovine serum) was prepared by a homomixer according to the method described in patent document 1. Thereto were added human megakaryoblastic leukemia MEG01 cells (manufactured by DS Pharma Biochemical) to a cell concentration of 100,000 cells/mL.

The above-mentioned cell suspension was dispensed to a 50 mL tube by 5 mL. As a chelator, 0.5 mL of an aqueous trisodium citrate dihydrate solution (3.8% (w/v) (129.2 mM)) was added, and the mixture was stirred by a vortex for 20 sec (N-20 M, manufactured by Nissin Rika). The final concentration of trisodium citrate at this time point was 0.35% (w/v) (12 mM). Thereafter, the cell suspension was statically stood at room temperature for 0 or 30 min.

Furthermore, D-PBS(−) (manufactured by Wako Pure Chemical Industries, Ltd.) was added by 20 mL or 0 mL (no addition) per one tube of cell suspension to dilute the suspension, and the mixture was mixed by inversion 20 times. Thereafter, for the filtration group, the suspension was passed through a nylon filter Cell Strainer (trade mark) (pore diameter 40 μm, manufactured by Becton, Dickinson and Company) 3 times to give a cell suspension. Each tube was subjected to a centrifugation treatment at 500 G for 10 min to precipitate the cells, and the supernatant was removed. The cells of each tube were resuspended in DMEM (1 mL), 10 μL was separated, mixed with an equal amount of Trypan Blue Stain 0.4% (manufactured by Invitrogen), the recovered viable cells were counted by a full automatic cell counter (TC20, manufactured by Bio-Rad) to measure the recovery rate.

As a positive control, human megakaryoblastic leukemia MEG01 cells (manufactured by DS Pharma Biochemical) were suspended in deacylated gellan gum-free DMEM at the above-mentioned concentration. Then, cells were precipitated by a centrifugation treatment at 500 G for 10 min, and the supernatant was removed. The cells were resuspended in DMEM (1 mL), 10 μL was separated, mixed with an equal amount of Trypan Blue Stain 0.4% (manufactured by Invitrogen), the recovered viable cells were counted by a full automatic cell counter (TC20, manufactured by Bio-Rad) to measure the recovery rate.

The cell recovery rate under respective conditions is shown in Table 7 where the recovery rate of the positive control is taken as 100. When the cell suspension was statically stood after addition of trisodium citrate, the cell recovery rate decreased; however, the filter filtration restored the cell recovery rate.

TABLE 7

|  | positive control | deacylated gellan gum addition group | | | | | | | |
|---|---|---|---|---|---|---|---|---|---|
| chelator | none | none | | | citric acid | | | | |
| vortex (sec) | 0 | 0 | | | 20 | | | | |
| standing time (min) | 0 | 0 | | 0 | | 30 | | | |
| dilution rate | 1 | 1 | | 5 | | | 5 | | |
| number of filtration | 0 | 0 | 0 | 3 | 0 | 3 | 0 | 3 | |
| cell recovery rate (% control) | 100.0 | 1.2 | 46.1 | 77.0 | 80.7 | 82.8 | 67.2 | 85.8 | |

[Example 8] Study of Chelator Addition Conditions

A medium composition of DMEM (manufactured by Wako Pure Chemical Industries, Ltd.) containing 0.015% (w/v) deacylated gellan gum (KELCOGEL CG-LA, manufactured by Sansho Co., Ltd.) and 10% (v/v) fetal bovine serum) was prepared by a homomixer according to the method described in patent document 1. Thereto were added human megakaryoblastic leukemia MEG01 cells (manufactured by DS Pharma Biochemical) to a cell concentration of 100,000 cells/mL.

The above-mentioned cell suspension was dispensed to a 50 mL tube by 5 mL. The following steps B and C were performed in the order of B→C or C→B.
B: Aqueous trisodium citrate dihydrate solution (0.5 mL) was added, and the mixture was stirred by a vortex for 20 sec (N-20 M, manufactured by Nissin Rika).
C: D-PBS(−) (manufactured by Wako Pure Chemical Industries, Ltd.) was added by 20 mL per one tube of cell suspension, and the mixture was mixed by inversion 20 times.

Thereafter, for the filtration group, the suspension was passed through a nylon filter Cell Strainer (trade mark) (pore diameter 40 μm, manufactured by Becton, Dickinson and Company) 3 times to give a cell suspension. Each tube was subjected to a centrifugation treatment at 500 G for 10 min to precipitate the cells, and the supernatant was removed. The cells of each tube were resuspended in DMEM (1 mL), 10 μL was separated, mixed with an equal amount of Trypan Blue Stain 0.4% (manufactured by Invitrogen), the recovered viable cells were counted by a full automatic cell counter (TC20, manufactured by Bio-Rad) to measure the recovery rate.

As a positive control, human megakaryoblastic leukemia MEG01 cells (manufactured by DS Pharma Biochemical) were suspended in deacylated gellan gum-free DMEM at the above-mentioned concentration. Then, cells were precipitated by a centrifugation treatment at 500 G for 10 min, and the supernatant was removed. The cells were resuspended in DMEM (1 mL), 10 μL was separated, mixed with an equal amount of Trypan Blue Stain 0.4% (manufactured by Invitrogen), the recovered viable cells were counted by a full automatic cell counter (TC20, manufactured by Bio-Rad) to measure the recovery rate.

The cell recovery rate under respective conditions is shown in Table 8 where the recovery rate of the positive control is taken as 100. The cell recovery rate was higher with a citric acid treatment prior to PBS dilution than a citric acid treatment after PBS dilution. However, a high cell recovery rate was achieved by filtration, irrespective of the order of steps B and C.

TABLE 8

|  | positive control | deacylated gellan gum addition group | | | | | | | | |
|---|---|---|---|---|---|---|---|---|---|---|
| chelator | none | none | | citric acid | | | | | | |
| dilution rate | 1 | 1 | | 5 | | | 5 | | | |
| order | — | — | | B→C | | C→B | | | C→B | |
| chelator final concentration (% (w/v)) | 0 | 0 | | 0.35 | | 0.07 | | | 0.35 | |
| standing time (min) | 0 | 0 | | 0 | | 30 | | | 30 | |
| number of filtration | 0 | 0 | 0 | 3 | 0 | 3 | 0 | 3 | 0 | 3 |
| cell recovery rate (% control) | 100.0 | 2.0 | 34.0 | 77.3 | 83.7 | 84.7 | 72.5 | 80.8 | 65.0 | 84.7 |

[Example 9] Study of Chelator Addition Conditions

A medium composition of DMEM (manufactured by Wako Pure Chemical Industries, Ltd.) containing 0.015% (w/v) deacylated gellan gum (KELCOGEL CG-LA, manufactured by Sansho Co., Ltd.) and 10% (v/v) fetal bovine serum) was prepared by a homomixer according to the method described in patent document 1. Thereto were added human megakaryoblastic leukemia MEG01 cells (manufactured by DS Pharma Biochemical) to a cell concentration of 100,000 cells/mL.

The above-mentioned cell suspension was dispensed to a 50 mL tube by 5 mL. The following steps A, B and C were performed in the order described in the following Table.
A: Passed through Cell Strainer (trade mark) (pore diameter 40 μm, manufactured by Becton, Dickinson and Company) 3 times.
B: Aqueous trisodium citrate dihydrate solution is added at a final concentration of 0.35% (w/v) (12 mM) and the mixture is stirred by vortex for 20 sec or gently blended manually for 30 sec.
C: 5-fold dilution with D-PBS(−).

The obtained cell suspension was subjected to a centrifugation treatment at 500 G for 10 min to precipitate the cells, and the supernatant was removed. The cells of each tube were resuspended in DMEM (1 mL), 10 μL was separated, mixed with an equal amount of Trypan Blue Stain 0.4% (manufactured by Invitrogen), the recovered viable cells were counted by a full automatic cell counter (TC20, manufactured by Bio-Rad) to measure the recovery rate.

As a positive control, human megakaryoblastic leukemia MEG01 cells (manufactured by DS Pharma Biochemical) were suspended in deacylated gellan gum-free DMEM at the above-mentioned concentration. Then, cells were precipitated by a centrifugation treatment at 500 G for 10 min, and the supernatant was removed. The cells were resuspended in DMEM (1 mL), 10 μL was separated, mixed with an equal amount of Trypan Blue Stain 0.4% (manufactured by Invitrogen), the recovered viable cells were counted by a full automatic cell counter (TC20, manufactured by Bio-Rad) to measure the recovery rate.

The cell recovery rate under respective conditions is shown in Table 9 where the recovery rate of the positive control is taken as 100. A high cell recovery rate was achieved by a combination of citric acid treatment, PBS dilution and filtration. In a group applied to a citric acid treatment after filtration, the cell recovery rate could not be measured, since cell pellets were formed by centrifugation, but the pellets floated.

TABLE 9

|  | positive control | deacylated gellan gum addition group | | | |
|---|---|---|---|---|---|
| A: filtration | x | x | ○ | | ○ |
| B: citric acid treatment | x | x | | ○ | |
| C: PBS dilution | x | x | ○ | | x |
| step order | — | — | B→C→A | C→A→B | A→B B→A |
| cell recovery rate (% control) | 100.0 | 4.3 | 77.1 | 83.4 | n.d. n.d. |

[Example 10] Cell Recovery Test Using Filter and Chelator

A medium composition of DMEM (manufactured by Wako Pure Chemical Industries, Ltd.) containing 0.015% (w/v) deacylated gellan gum (KELCOGEL CG-LA, manufactured by Sansho Co., Ltd.) and 10% (v/v) fetal bovine serum) was prepared by a homomixer according to the method described in patent document 1. Thereto were added human megakaryoblastic leukemia MEG01 cells (manufactured by DS Pharma Biochemical) to a cell concentration of 100,000 cells/mL.

The above-mentioned cell suspension was dispensed to a 50 mL tube by 5 mL. The cell recovery rate was evaluated by the presence or absence of a pre-treatment before centrifugation recovery. In a group with a pre-treatment, the suspension was passed through a nylon filter Cell Strainer (trade mark)(pore diameter 40 μm, manufactured by Becton, Dickinson and Company) 3 times. Then, 3.8% (w/v) (129.2 mM) aqueous trisodium citrate dihydrate solution (0.5 mL) was added (final concentration 0.35% (w/v) (12 mM)), and the mixture was stirred manually for 30 sec to the extent free from foaming. Furthermore, 5 mL of D-PBS(−) (manufactured by Wako Pure Chemical Industries, Ltd.) was added to 5 mL of cell suspension to dilute the suspension (2-fold dilution), and the mixture was mixed by inversion 20 times. As a positive control, human megakaryoblastic leukemia MEG01 cells (manufactured by DS Pharma Biochemical) were suspended in deacylated gellan gum-free DMEM at the above-mentioned concentration.

Each tube was subjected to a centrifugation treatment at 500 G for 10 min to precipitate the cells, and the supernatant was removed. The cells of each tube were resuspended in DMEM (1 mL), 10 μL was separated, mixed with an equal amount of Trypan Blue Stain 0.4% (manufactured by Invitrogen), the recovered viable cells were counted by a full automatic cell counter (TC20, manufactured by Bio-Rad) to measure the recovery rate.

The cell recovery rate under respective conditions is shown in Table 10 where the recovery rate of the positive control is taken as 100. In the group applied to the aforementioned pre-treatment, a recovery rate of 90% was shown, and not less than 10 times as many cells as that in the group free of the treatment were obtained. This has revealed usefulness of a cell recovery method using a combination of filtration, chelate treatment and dilution.

TABLE 10

|  | positive control | deacylated gellan gum addition group | |
|---|---|---|---|
| number of filtration | 0 | 0 | 3 |
| additive | none | none | citric acid 3Na |
| dilution rate | 1 | 1 | 2 |
| cell recovery rate (% control) | 100 | 8 | 91 |

[Example 11] Effect of Protein in Medium on Cell Recovery Method Using Chelator A medium composition of DMEM (manufactured by Wako Pure Chemical Industries, Ltd.) containing 0.015% (w/v) deacylated gellan gum (KELCOGEL CG-LA, manufactured by Sansho Co., Ltd.) was prepared by a homomixer according to the method of patent document 1. To the above-mentioned medium was added 0% (no addition) or 10% (v/v) fetal bovine serum (FBS), or 0.10% (w/v) bovine serum albumin (BSA). To each prepared medium were added human megakaryoblastic leukemia MEG01 cells (manufactured by DS Pharma Biochemical) to a cell concentration of 100,000 cells/mL, and the cell suspension was dispensed to a 50 mL tube by 5 mL. Then, 3.8% (w/v) aqueous trisodium citrate solution (0 mL or 0.5 mL) was added (final concentration 0.35% (w/v)), and the mixture was stirred for 20 sec by a vortex. Furthermore, 20 mL of D-PBS(−) (manufactured by Wako Pure Chemical Industries, Ltd.) was added to 5 mL of cell suspension to dilute the suspension (5-fold dilution), and the mixture was mixed by inversion 20 times. Each tube was subjected to a centrifugation treatment at 500 G for 10 min to precipitate the cells, and the supernatant was removed. The cells of each tube were resuspended in DMEM (1 mL), 10 μL was separated, mixed with an equal amount of Trypan Blue Stain 0.4% (manufactured by Invitrogen), the recovered viable cells were counted by a full automatic cell counter (TC20, manufactured by Bio-Rad) to measure the recovery rate. As a positive control, human megakaryoblastic leukemia MEG01 cells (manufactured by DS Pharma Biochemical) were suspended in deacylated gellan gum-free DMEM at the above-mentioned concentration.

Each tube was subjected to a centrifugation treatment at 500 G for 10 min to precipitate the cells, and the supernatant was removed. The cells of each tube were resuspended in DMEM (1 mL), 10 μL was separated, mixed with an equal amount of Trypan Blue Stain 0.4% (manufactured by Invitrogen), the recovered viable cells were counted by a full automatic cell counter (TC20, manufactured by Bio-Rad) to measure the recovery rate.

The cell recovery rate under respective conditions is shown in Table 11 where the recovery rate of the positive control is taken as 100. The results have clarified that the presence of protein such as FBS, BSA and the like in the medium enhances the cell recovery rate-increasing effect afforded by the addition of chelator or dilution. In addition, when 20% (v/v) FBS or 0.20% (w/v) BSA was added, a high cell recovery rate similar to that when 10% (v/v) FBS, or 0.10% (w/v) BSA was added was also achieved by the citric acid treatment and/or dilution treatment.

TABLE 11

|  | positive control | deacylated gellan gum addition group | | | | | |
|---|---|---|---|---|---|---|---|
| additive | 10% FBS | — | — | 10% FBS | | 0.1% BSA | |
| citric acid 3Na | x | x | ○ | x | ○ | x | ○ |
| dilution rate | 1 | 5 | 5 | 5 | 5 | 5 | 5 |
| cell recovery rate (% control) | 100 | 31 | 28 | 46 | 70 | 42 | 59 |

[Example 12] Effect of Filtration in Cell Recovery

A medium composition of DMEM (manufactured by Wako Pure Chemical Industries, Ltd.) containing 0.015% (w/v) deacylated gellan gum (KELCOGEL CG-LA, manufactured by Sansho Co., Ltd.) and 10% (v/v) fetal bovine serum) was prepared by a homomixer according to the method of patent document 1. Thereto were added human megakaryoblastic leukemia MEG01 cells (manufactured by DS Pharma Biochemical) to a cell concentration of 100,000 cells/mL. The above-mentioned cell suspension was dispensed by 5 mL in a 50 mL tube, and filtration was performed 3 times with any of the various filters shown below.

filter No. 1: SpectraMesh (trade mark) manufactured by Spectrum Laboratories, polyester, 37 μm, filter No. 2: Filcon S (trade mark) manufactured by AS ONE: polyethylene, 20 μm, filter No. 3: Filcon S (trade mark) manufactured by AS ONE: polyethylene, 30 μm, filter No. 4: Filcon S (trade mark) manufactured by AS ONE: polyethylene, 100 μm, filter No. 5: Cell Strainer (trade mark) manufactured by Becton, Dickinson and Company: nylon, pore diameter 40 μm, filter No. 6: Cell Strainer (trade mark) manufactured by Becton, Dickinson and Company: nylon, pore diameter 100 μm, filter No. 7: glass filter plate manufactured by Fuji Rika, glass, pore diameter 40-50 μm.

Furthermore, 20 mL of D-PBS(−) (manufactured by Wako Pure Chemical Industries, Ltd.) was added to 5 mL of cell suspension to dilute the suspension (5-fold dilution), and the mixture was mixed by inversion 20 times. As a positive control, human megakaryoblastic leukemia MEG01 cells (manufactured by DS Pharma Biochemical) were suspended in deacylated gellan gum-free DMEM at the above-mentioned concentration.

Each tube was subjected to a centrifugation treatment at 500 G for 10 min to precipitate the cells, and the supernatant was removed. The cells of each tube were resuspended in DMEM (1 mL), 10 μL was separated, mixed with an equal amount of Trypan Blue Stain 0.4% (manufactured by Invitrogen), the recovered viable cells were counted by a full automatic cell counter (TC20, manufactured by Bio-Rad) to measure the recovery rate.

The cell recovery rate under respective conditions is shown in Table 12 where the recovery rate of the positive control is taken as 100. From the results, filters made of any material (30-40 μm diameter) showed a cell recovery rate of about 80%.

TABLE 12

|  | positive control | | deacylated gellan gum addition group | | | | | | |
|---|---|---|---|---|---|---|---|---|---|
| filter | — | — | No. 1 | No. 2 | No. 3 | No. 4 | No. 5 | No. 6 | No. 7 |
| material | — | — | polyester | polyethylene | polyethylene | polyethylene | nylon | nylon | glass |
| pore diameter (μm) | — | — | 37 | 20 | 30 | 100 | 40 | 100 | 40-50 |
| cell recovery rate (% control) | 100 | 2 | 77 | 74 | 84 | 71 | 80 | 74 | 69 |

[Example 13] Cell Recovery Test Using Filter (Multiple Layered) and Chelator

A medium composition of DMEM (manufactured by Wako Pure Chemical Industries, Ltd.) containing 0.015% (w/v) deacylated gellan gum (KELCOGEL CG-LA, manufactured by Sansho Co., Ltd.) and 10% (v/v) fetal bovine serum) was prepared by a homomixer according to the method described in patent document 1. Thereto were added human megakaryoblastic leukemia MEG01 cells (manufactured by DS Pharma Biochemical) to a cell concentration of 100,000 cells/mL. The above-mentioned cell suspension was dispensed to a 50 mL tube by 5 mL, and passed 3 times through Filcon S (trade mark) (pore diameter 30 μm, manufactured by AS ONE), or passed once through 3 sheets of filter membrane in the filter, which were layered together and set on a filter holder (Nihon Millipore K.K., model number: XX3001240). Then, 3.8% (w/v) (129.2 mM) aqueous trisodium citrate dihydrate solution (0 mL (no addition) or 0.5 mL) was added (final concentration 0.35% (w/v) (12 mM)), and the mixture was stirred by vortex for 20 sec. Furthermore, 0 mL (no addition) or 20 mL of D-PBS(−) (manufactured by Wako Pure Chemical Industries, Ltd.) was added to 5 mL of cell suspension to dilute the suspension (5-fold dilution), and the mixture was mixed by inversion 20 times. As a positive control, human megakaryoblastic leukemia MEG01 cells (manufactured by DS Pharma Biochemical) were suspended in deacylated gellan gum-free DMEM at the above-mentioned concentration.

Each tube was subjected to a centrifugation treatment at 500 G for 10 min to precipitate the cells, and the supernatant was removed. The cells of each tube were resuspended in DMEM (1 mL), 10 μL was separated, mixed with an equal amount of Trypan Blue Stain 0.4% (manufactured by Invitrogen), the recovered viable cells were counted by a full automatic cell counter (TC20, manufactured by Bio-Rad) to measure the recovery rate.

The cell recovery rate under respective conditions is shown in Table 13 where the recovery rate of the positive control is taken as 100. The results show that a cell recovery rate of the same level as three times of filtration through a single layer was obtained by using three filters layered together.

TABLE 13

|  | positive control | | deacylated gellan gum addition group | |
|---|---|---|---|---|
| number of filter | 0 | 0 | 1 | 3 |
| number of filtration | 0 | 0 | 3 | 1 |
| citric acid 3Na | X | X | ○ | ○ |
| dilution rate | 1 | 1 | 5 | 5 |
| cell recovery rate (% control) | 100 | 3 | 85 | 88 |

[Example 14] Study of Dilution Rate and Reduction of Centrifugal Force by Chelator A medium composition of DMEM (manufactured by Wako Pure Chemical Industries, Ltd.) containing 0.015% (w/v) deacylated gellan gum (KELCOGEL CG-LA, manufactured by Sansho Co., Ltd.) and 10% (v/v) fetal bovine serum) was prepared by a homomixer according to the method described in patent document 1. Thereto were added human megakaryoblastic leukemia MEG01 cells (manufactured by DS Pharma Biochemical) to a cell concentration of 100,000 cells/mL. The above-mentioned cell suspension was dispensed to a 50 mL tube by 5 mL, and passed once through 3 sheets of filter membrane in Filcon S (trade mark) (pore diameter 30 μm, manufactured by AS ONE), which were layered together and set on a filter holder (Nihon Millipore K.K., model number: XX3001240). Then, 3.8% (w/v) (129.2 mM) aqueous trisodium citrate dihydrate solution (0 mL (no addition) or 0.5 mL) was added (final concentration 0.35% (w/v) (12 mM)), and the mixture was stirred by vortex for 20 sec. Furthermore, 0 mL (no addition), 5 mL (2-fold dilution) or 20 mL (5-fold dilution) of D-PBS(−) (manufactured by Wako Pure Chemical Industries, Ltd.) was added to 5 mL of cell suspension to dilute the suspension, and the mixture was mixed by inversion 20 times. As a positive control, human megakaryoblastic leukemia MEG01 cells (manufactured by DS Pharma Biochemical) were suspended in deacylated gellan gum-free DMEM at the above-mentioned concentration.

Each tube was subjected to a centrifugation treatment at 300 G or 500 G for 10 min to precipitate the cells, and the supernatant was removed. The cells of each tube were resuspended in DMEM (1 mL), 10 μL was separated, mixed with an equal amount of Trypan Blue Stain 0.4% (manufactured by Invitrogen), the recovered viable cells were counted by a full automatic cell counter (TC20, manufactured by Bio-Rad) to measure the recovery rate.

The cell recovery rate under respective conditions is shown in Table 14 where the recovery rate of the positive control is taken as 100. When the dilution rate became lower, the cell recovery rate decreased. However, when citric acid was added, the rate was improved and, even when the centrifugal force was reduced to 300 G, not less than 70% of recovery rate was obtained.

TABLE 14

|  | positive control | deacylated gellan gum addition group | | |
|---|---|---|---|---|
| filtration | X | ○ | ○ | ○ |
| citric acid 3Na | X | X | X | ○ |
| dilution rate | 1 | 5 | 2 | 2 |
| centrifugal force (G) | 500 | 500 | 500 | 300 |
| cell recovery rate (% control) | 100 | 86 | 35 | 74 |

[Example 15] Recovery of Lymphoid Cells by Using Filter and Chelator

A medium composition of DMEM (manufactured by Wako Pure Chemical Industries, Ltd.) or RPMI1640 medium (manufactured by Wako Pure Chemical Industries, Ltd.) containing 0.015% or 0.020% (w/v) deacylated gellan gum (KELCOGEL CG-LA, manufactured by Sansho Co., Ltd.) and 10% (v/v) fetal bovine serum was prepared by a homomixer according to the method described in patent document 1. To the above-mentioned medium were added human T-cell leukemia Jurkat cells (manufactured by American Type Culture Collection, Clone E6-1) to a cell concentration of 100,000 cells/mL. The above-mentioned cell suspension was dispensed to a 50 mL tube by 5 mL, and passed once through 3 sheets of Filcon S (trade mark) (pore diameter 30 μm, manufactured by AS ONE), which were layered together and set on a filter holder (Nihon Millipore K.K., model number: XX3001240). Then, 3.8% (w/v) (129.2 mM) aqueous trisodium citrate dihydrate solution (0 mL (no addition) or 0.5 mL) was added (final concentration 0.35% (w/v) (12 mM)), and the mixture was stirred by vortex for 20 sec. Furthermore, 0 mL (no addition) or 20 mL (5-fold dilution) of D-PBS(−) (manufactured by Wako Pure Chemical Industries, Ltd.) was added to 5 mL of cell suspension to dilute the suspension, and the mixture was mixed by inversion 20 times. As a positive control, Jurkat cells (manufactured by American Type Culture Collection, Clone E6-1) were suspended in deacylated gellan gum-free DMEM at the above-mentioned concentration.

Each tube was subjected to a centrifugation treatment at 500 G for 10 min to precipitate the cells, and the supernatant was removed. The cells of each tube were resuspended in DMEM (1 mL), 10 μL was separated, mixed with an equal amount of Trypan Blue Stain 0.4% (manufactured by Invitrogen), the recovered viable cells were counted by a full automatic cell counter (TC20, manufactured by Bio-Rad) to measure the recovery rate.

The cell recovery rate under respective conditions is shown in Table 15 where the recovery rate of the positive control is taken as 100. By combined use of filtration and chelator, not less than 95% of lymphoid cells could be recovered from the deacylated gellan gum-containing medium.

TABLE 15

|  | positive control | deacylated gellan gum addition group | |
|---|---|---|---|
| deacylated gellan gum concentration/basal medium | —/DMEM | 0.015%/DMEM | 0.020%/RPMI |
| filtration | X | X | ○ | ○ |
| citric acid 3Na | X | X | ○ | ○ |
| dilution rate | 1 | 1 | 5 | 5 |
| cell recovery rate (% control) | 100 | 5 | 99 | 97 |

[Example 16] Evaluation of Cell Proliferation after Recovery Using Filter and Chelator Human T-cell leukemia Jurkat cells (manufactured by American Type Culture Collection, Clone E6-1) recovered from 0.020% deacylated gellan gum-containing RPMI1640 medium (manufactured by Wako Pure Chemical Industries, Ltd.) by using a filter and citric acid 3Na in the same manner as in [Example 15] were added to 10% (v/v) fetal bovine serum-containing RPMI1640 medium (manufactured by Wako Pure Chemical Industries, Ltd.) to a cell concentration of 100,000 cells/mL. As a positive control, cells free from a cell recovery treatment (filtration, chelator addition, centrifugation treatment) were suspended in the same medium at the same concentration.

The above-mentioned cell suspension was dispensed to a 25 cm$^2$ cell culture flask (manufactured by Corning Incorporated) by 10 mL, and cultured in a 5% $CO_2$ incubator at 37° C. up to 6 days.

After culture, 10 μL was separated from the cell suspension, mixed with an equal amount of Trypan Blue Stain 0.4% (manufactured by Invitrogen), the viable cells were counted by a full automatic cell counter (TC20, manufactured by Bio-Rad).

The cell proliferation evaluation results are shown in Table 16. The cell proliferation rate was of the same level irrespective of the presence or absence of a recovery treatment, and cytotoxicity due to a recovery treatment was not observed.

TABLE 16

|  | positive control | deacylated gellan gum addition group |
|---|---|---|
| recovery treatment | X | ○ |
|  | viable cells ($\times 10^5$/mL) | |
| day 0 | 1 | 1 |
| day 2 | 2.2 | 2.1 |
| day 6 | 25.1 | 28.0 |

INDUSTRIAL APPLICABILITY

According to the present invention, animal or plant cells and/or tissues can be more efficiently recovered from the culture preparation obtained after the animal or plant cells and/or tissues are cultured in a medium composition which enables culture of the cells or tissues in suspension.

The contents disclosed in any publication cited herein, including patents, patent applications and scientific literatures, are hereby incorporated in their entireties by reference, to the extent that they have been disclosed herein.

This application is based on patent application Nos. 2014-183687 (filing date: Sep. 9, 2014) and 2015-110331 (filing date: May 29, 2015), filed in Japan, the contents of which are incorporated in full herein.

The invention claimed is:

1. A method of isolating cells or tissues, which method comprises
   (A1) passing a culture preparation of the cells or tissues in a medium composition, which comprises a polymer compound having an anionic functional group that enables culture of the cells or tissues in suspension, through a filter having fine pores with a diameter of 5-500 μm,
   (A2) isolating cells or tissues from the filtrate obtained in step (A1), and
   (B) adding a chelator to the culture preparation, wherein the chelator is citric acid or a salt thereof.

2. The method according to claim 1, wherein the polymer compound is an acidic polysaccharide having an anionic functional group.

3. The method according to claim 1, wherein the medium composition comprises deacylated gellan gum or a salt thereof.

4. The method according to claim 1, wherein the fine pores of the filter have a diameter of 20-100 μm.

5. The method according to claim 1, wherein the culture preparation is passed through the filter plural times.

6. The method according to claim 1, wherein, after addition of the chelator, the culture preparation is stirred for not less than 10 min.

7. The method according to claim 1, further comprising (C) diluting the culture preparation with a physiological aqueous solution, wherein the physiological aqueous solution is substantially free of calcium ion and magnesium ion.

8. The method according to claim 7, wherein the steps (A1), (A2), (B) and (C) are performed in the order of (A1), (A2), (B), (C).

9. The method according to claim 7, wherein the polymer compound is an acidic polysaccharide having an anionic functional group.

10. The method according to claim 7, wherein the medium composition comprises deacylated gellan gum or a salt thereof.

11. The method according to claim 7, wherein the fine pores of the filter have a diameter of 20-100 μm.

12. The method according to claim 7, wherein the culture preparation is passed through the filter plural times.

13. The method according to claim 7, wherein, after addition of the chelator, the culture preparation is stirred for not less than 10 min.

14. The method according to claim 7, wherein the physiological aqueous solution is phosphate buffered saline.

15. A method of isolating cells or tissues, which method comprises
    (A1) passing a culture preparation of the cells or tissues in a medium composition, which comprises a polymer compound having an anionic functional group that enables culture of the cells or tissues in suspension, through a filter having fine pores with a diameter of 5-500 μm,
    (A2) isolating cells or tissues from the filtrate obtained in step (A1), and
    (C) diluting the culture preparation with a physiological aqueous solution, wherein the physiological aqueous solution is substantially free of calcium ion and magnesium ion.

16. The method according to claim 15, wherein the polymer compound is an acidic polysaccharide having an anionic functional group.

17. The method according to claim 15, wherein the medium composition comprises deacylated gellan gum or a salt thereof.

18. The method according to claim 15, wherein the culture preparation is passed through the filter plural times.

19. The method according to claim 15, wherein the fine pores of the filter have a diameter of 20-100 μm.

20. The method according to claim 15, wherein the physiological aqueous solution is phosphate buffered saline.

* * * * *